(12) United States Patent
Kaula et al.

(10) Patent No.: US 9,615,788 B2
(45) Date of Patent: Apr. 11, 2017

(54) METHOD AND SYSTEM OF PRODUCING 2D REPRESENTATIONS OF 3D PAIN AND STIMULATION MAPS AND IMPLANT MODELS ON A CLINICIAN PROGRAMMER

(71) Applicant: Greatbatch Ltd., Clarence, NY (US)

(72) Inventors: Norbert Kaula, Arvada, CO (US); Yohannes Iyassu, Denver, CO (US)

(73) Assignee: Nuvectra Corporation, Plano, TX (US)

( * ) Notice: Subject to any disclaimer, the term of this patent is extended or adjusted under 35 U.S.C. 154(b) by 327 days.

(21) Appl. No.: 13/973,219

(22) Filed: Aug. 22, 2013

(65) Prior Publication Data
US 2014/0063003 A1   Mar. 6, 2014

Related U.S. Application Data

(60) Provisional application No. 61/695,407, filed on Aug. 31, 2012, provisional application No. 61/695,721, (Continued)

(51) Int. Cl.
*A61B 5/00* (2006.01)
*G06T 15/04* (2011.01)
(Continued)

(52) U.S. Cl.
CPC ............ *A61B 5/4824* (2013.01); *G06T 15/00* (2013.01); *G06T 15/04* (2013.01); *G06T 19/00* (2013.01);
(Continued)

(58) Field of Classification Search
None
See application file for complete search history.

(56) References Cited

U.S. PATENT DOCUMENTS 4,432,360 A   2/1984   Mumford et al.
5,286,202 A   2/1994   De Gyarfas et al.
(Continued)

FOREIGN PATENT DOCUMENTS

EP   1192972   4/2002
EP   2277586   1/2011
(Continued)

OTHER PUBLICATIONS

Shenchang Eric Chen, "QuickTime VR: An Image-Based Approach to Virtual Environment Navigation", Aug. 11, 1995, ACM, SIGGRAPH '95 Proceedings of the 22$^{nd}$ annual conference on computer graphics and interactive techniques, pp. 29-38.*
(Continued)

*Primary Examiner* — Robert Bader
(74) *Attorney, Agent, or Firm* — Haynes and Boone, LLP; Eric Li

(57) ABSTRACT

The present disclosure involves an electronic device for visualizing a sensation experienced by a patient. The electronic device includes a touchscreen display configured to receive a tactile input from a user and display a visual output. The electronic device includes a memory storage component configured to store programming code. The electronic device includes a computer processor configured to execute the programming code to perform the following tasks: generating, in response to the tactile input from the user, a three-dimensional (3D) sensation map that represents the sensation experienced by the patient; deriving a two-dimensional (2D) sensation map based on the 3D sensation map, wherein the 2D sensation map contains substantially less data than the 3D sensation map; and sending the 2D sensation map over a network to facilitate a reconstruction of the 3D sensation map using the 2D sensation map.

37 Claims, 27 Drawing Sheets

Related U.S. Application Data filed on Aug. 31, 2012, provisional application No. 61/695,676, filed on Aug. 31, 2012, provisional application No. 61/824,296, filed on May 16, 2013.

(51) Int. Cl.
  *G06T 15/00* (2011.01)
  *G06T 19/00* (2011.01)
  *A61N 1/36* (2006.01)
  *A61N 1/372* (2006.01)

(52) U.S. Cl.
  CPC ...... *A61N 1/36128* (2013.01); *A61N 1/37247* (2013.01); *G06T 2200/24* (2013.01); *G06T 2210/41* (2013.01)

(56) References Cited

U.S. PATENT DOCUMENTS

| | | | |
|---|---|---|---|
| 5,304,206 A | 4/1994 | Baker, Jr. et al. | |
| 5,312,446 A | 5/1994 | Holschbach et al. | |
| 5,370,672 A | 12/1994 | Fowler et al. | |
| 5,383,914 A | 1/1995 | O'Phelan | |
| 5,421,830 A | 6/1995 | Epstein et al. | |
| 5,628,776 A | 5/1997 | Paul et al. | |
| 5,713,937 A | 2/1998 | Nappholz et al. | |
| 5,722,999 A | 3/1998 | Snell | |
| 5,724,996 A | 3/1998 | Piunti | |
| 5,819,740 A | 10/1998 | Muhlenberg | |
| 5,879,374 A | 3/1999 | Powers et al. | |
| 5,905,500 A | 5/1999 | Kamen et al. | |
| 5,938,690 A | 8/1999 | Law et al. | |
| 6,016,447 A | 1/2000 | Juran et al. | |
| 6,016,448 A | 1/2000 | Busacker et al. | |
| 6,052,624 A | 4/2000 | Mann | |
| 6,083,156 A | 7/2000 | Lisiecki | |
| 6,148,233 A | 11/2000 | Owen et al. | |
| 6,154,675 A | 11/2000 | Juran et al. | |
| 6,216,036 B1 | 4/2001 | Jenkins et al. | |
| 6,246,414 B1 | 6/2001 | Kawasaki | |
| 6,249,705 B1 | 6/2001 | Snell | |
| 6,278,890 B1 | 8/2001 | Chassaing et al. | |
| 6,307,554 B1 | 10/2001 | Arai et al. | |
| 6,308,102 B1 | 10/2001 | Sieracki et al. | |
| 6,345,200 B1 | 2/2002 | Mouchawar et al. | |
| 6,386,882 B1 | 5/2002 | Linberg | |
| 6,442,432 B2 | 8/2002 | Lee | |
| 6,525,727 B1 | 2/2003 | Junkins et al. | |
| 6,529,195 B1 * | 3/2003 | Eberlein | A61B 5/0002 345/441 |
| 6,564,104 B2 | 5/2003 | Nelson et al. | |
| 6,587,104 B1 | 7/2003 | Hoppe | |
| 6,611,267 B2 | 8/2003 | Migdal et al. | |
| 6,622,048 B1 | 9/2003 | Mann et al. | |
| 6,669,631 B2 | 12/2003 | Norris et al. | |
| 6,786,405 B2 | 9/2004 | Wiedenhoefer | |
| 6,852,080 B2 | 2/2005 | Bardy | |
| 6,882,982 B2 | 4/2005 | McMenimen et al. | |
| 6,895,280 B2 | 5/2005 | Meadows et al. | |
| 6,920,360 B2 | 7/2005 | Lee et al. | |
| 6,931,155 B1 | 8/2005 | Gioia | |
| 6,961,448 B2 | 11/2005 | Nichols et al. | |
| 6,961,617 B1 | 11/2005 | Snell | |
| 7,003,349 B1 | 2/2006 | Andersson et al. | |
| 7,034,823 B2 | 4/2006 | Dunnet | |
| 7,058,453 B2 | 6/2006 | Nelson et al. | |
| 7,060,030 B2 | 6/2006 | Von Arx et al. | |
| 7,065,409 B2 | 6/2006 | Mazar | |
| 7,066,910 B2 | 6/2006 | Bauhahn et al. | |
| 7,076,303 B2 | 7/2006 | Linberg | |
| 7,087,015 B1 | 8/2006 | Comrie et al. | |
| 7,092,761 B1 | 8/2006 | Cappa et al. | |
| 7,107,102 B2 | 9/2006 | Daignault et al. | |
| 7,142,923 B2 | 11/2006 | North et al. | |
| 7,181,286 B2 | 2/2007 | Sieracki et al. | |
| 7,181,505 B2 | 2/2007 | Haller et al. | |
| 7,184,837 B2 | 2/2007 | Goetz | |
| 7,239,926 B2 | 7/2007 | Goetz | |
| 7,266,412 B2 | 9/2007 | Stypulkowski | |
| 7,299,085 B2 | 11/2007 | Bergelson et al. | |
| 7,302,373 B2 * | 11/2007 | Fleury | G01V 11/00 345/419 |
| 7,359,751 B1 | 4/2008 | Erickson et al. | |
| 7,373,204 B2 | 5/2008 | Gelfand et al. | |
| 7,440,806 B1 | 10/2008 | Whitehurst et al. | |
| 7,452,336 B2 | 11/2008 | Thompson | |
| 7,463,927 B1 | 12/2008 | Chaouat | |
| 7,474,223 B2 | 1/2009 | Nycz et al. | |
| 7,481,759 B2 | 1/2009 | Whitehurst et al. | |
| 7,489,970 B2 | 2/2009 | Lee et al. | |
| 7,496,403 B2 | 2/2009 | Cao et al. | |
| 7,499,048 B2 | 3/2009 | Sieracki et al. | |
| 7,505,815 B2 | 3/2009 | Lee et al. | |
| 7,551,960 B2 | 6/2009 | Forsberg et al. | |
| 7,602,384 B2 | 10/2009 | Rosenberg et al. | |
| 7,617,002 B2 | 11/2009 | Goetz | |
| 7,627,372 B2 | 12/2009 | Vaisnys et al. | |
| 7,640,059 B2 | 12/2009 | Forsberg et al. | |
| 7,657,317 B2 | 2/2010 | Thacker et al. | |
| 7,685,005 B2 | 3/2010 | Riff et al. | |
| 7,711,603 B2 | 5/2010 | Vanker et al. | |
| 7,720,549 B2 | 5/2010 | Schroeppel et al. | |
| 7,747,330 B2 | 6/2010 | Nolan et al. | |
| 7,774,067 B2 | 8/2010 | Keacher et al. | |
| 7,778,710 B2 | 8/2010 | Propato | |
| 7,801,596 B2 | 9/2010 | Fischell et al. | |
| 7,801,611 B2 | 9/2010 | Persen et al. | |
| 7,805,199 B2 | 9/2010 | KenKnight et al. | |
| 7,822,483 B2 | 10/2010 | Stone et al. | |
| 7,853,323 B2 | 12/2010 | Goetz | |
| 7,885,712 B2 | 2/2011 | Goetz et al. | |
| 7,890,180 B2 | 2/2011 | Quiles et al. | |
| 7,928,995 B2 | 4/2011 | Daignault | |
| 7,934,508 B2 | 5/2011 | Behm | |
| 7,940,933 B2 | 5/2011 | Corndorf | |
| 7,953,492 B2 | 5/2011 | Corndorf | |
| 7,953,612 B1 | 5/2011 | Palmese et al. | |
| 7,957,808 B2 | 6/2011 | Dawant et al. | |
| 7,978,062 B2 | 7/2011 | LaLonde et al. | |
| 7,991,482 B2 | 8/2011 | Bradley | |
| 8,014,863 B2 | 9/2011 | Zhang et al. | |
| 8,021,298 B2 | 9/2011 | Barid et al. | |
| 8,027,726 B2 | 9/2011 | Ternes | |
| 8,046,241 B1 | 10/2011 | Dodson | |
| 8,060,216 B2 | 11/2011 | Greenberg et al. | |
| 8,068,915 B2 | 11/2011 | Lee et al. | |
| 8,068,918 B2 | 11/2011 | Vallapureddy et al. | |
| 8,078,440 B2 | 12/2011 | Otto et al. | |
| 8,082,162 B2 | 12/2011 | Flood | |
| 8,121,702 B2 | 2/2012 | King | |
| 8,135,566 B2 | 3/2012 | Marshall et al. | |
| 8,140,160 B2 | 3/2012 | Pless et al. | |
| 8,140,167 B2 | 3/2012 | Donders et al. | |
| 8,160,328 B2 | 4/2012 | Goetz et al. | |
| 8,160,704 B2 | 4/2012 | Freeberg | |
| 8,165,385 B2 | 4/2012 | Reeves et al. | |
| 8,187,015 B2 | 5/2012 | Boyd et al. | |
| 8,200,324 B2 | 6/2012 | Shen et al. | |
| 8,200,340 B2 | 6/2012 | Skelton et al. | |
| 8,219,206 B2 | 7/2012 | Skelton et al. | |
| 8,233,991 B2 | 7/2012 | Woods et al. | |
| 8,246,680 B2 | 8/2012 | Betz et al. | |
| 8,249,713 B2 | 8/2012 | Fang et al. | |
| 8,255,060 B2 | 8/2012 | Goetz et al. | |
| 8,323,218 B2 | 12/2012 | Davis et al. | |
| 8,326,433 B2 | 12/2012 | Blum et al. | |
| 8,340,775 B1 | 12/2012 | Cullen et al. | |
| 8,382,666 B1 | 2/2013 | Mao et al. | |
| 8,386,032 B2 | 2/2013 | Bachinski et al. | |
| 8,401,666 B2 | 3/2013 | Skelton et al. | |
| 8,428,727 B2 | 4/2013 | Bolea et al. | |
| 2001/0026272 A1 * | 10/2001 | Feld | A41H 3/007 345/419 |
| 2001/0037220 A1 | 11/2001 | Merry et al. | |

(56) References Cited

U.S. PATENT DOCUMENTS

| | | |
|---|---|---|
| 2003/0076301 A1 | 4/2003 | Tsuk et al. |
| 2003/0107572 A1 | 6/2003 | Smith et al. |
| 2003/0139652 A1 | 7/2003 | Kang et al. |
| 2003/0171911 A1 | 9/2003 | Fairweather |
| 2003/0177031 A1 | 9/2003 | Malek |
| 2004/0088374 A1 | 5/2004 | Webb et al. |
| 2004/0122477 A1 | 6/2004 | Whitehurst et al. |
| 2004/0136578 A1* | 7/2004 | Sieracki ............... A61B 5/00 382/128 |
| 2004/0210273 A1 | 10/2004 | Wang |
| 2005/0107831 A1 | 5/2005 | Hill et al. |
| 2005/0149356 A1 | 7/2005 | Cyr et al. |
| 2005/0168460 A1 | 8/2005 | Razdan et al. |
| 2005/0192972 A1* | 9/2005 | Daignault, Jr. ........ A61N 1/08 |
| 2005/0277872 A1 | 12/2005 | Colby et al. |
| 2006/0089888 A1 | 4/2006 | Roger |
| 2006/0100832 A1 | 5/2006 | Bowman |
| 2006/0241720 A1 | 10/2006 | Woods et al. |
| 2006/0242159 A1 | 10/2006 | Bishop et al. |
| 2006/0282168 A1 | 12/2006 | Sherman et al. |
| 2007/0078497 A1 | 4/2007 | Vandanacker |
| 2007/0093998 A1 | 4/2007 | El-Baroudi et al. |
| 2007/0179349 A1 | 8/2007 | Hoyme et al. |
| 2007/0203537 A1 | 8/2007 | Goetz et al. |
| 2007/0203538 A1 | 8/2007 | Stone et al. |
| 2007/0203543 A1 | 8/2007 | Stone et al. |
| 2007/0213790 A1 | 9/2007 | Nolan et al. |
| 2008/0004675 A1 | 1/2008 | King et al. |
| 2008/0033303 A1 | 2/2008 | Wariar et al. |
| 2008/0046036 A1 | 2/2008 | King et al. |
| 2008/0140161 A1 | 6/2008 | Goetz et al. |
| 2008/0177362 A1 | 7/2008 | Phillips et al. |
| 2008/0218517 A1 | 9/2008 | Holmdahl |
| 2008/0262565 A1 | 10/2008 | Bentwich |
| 2009/0005649 A1* | 1/2009 | Baird .................... A61B 5/00 600/300 |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0089034 A1 | 4/2009 | Penney et al. |
| 2009/0099624 A1 | 4/2009 | Kokones et al. |
| 2009/0132009 A1 | 5/2009 | Torgenson et al. |
| 2009/0136094 A1 | 5/2009 | Driver et al. |
| 2009/0196471 A1 | 8/2009 | Goetz et al. |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennet et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0196455 A1 | 8/2011 | Sieracki et al. |
| 2011/0224523 A1 | 9/2011 | Burdiman |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0192874 A1 | 8/2012 | Bolea et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Conner et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296293 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| WO | WO 9959106 | 11/1999 |
| WO | WO 0209808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Shenchang Eric Chen, Lance Williams, "View Interpolation for Image Synthesis", Aug. 6, 1993, ACM, SIGGRAPH '93 Proceedings of the 20$^{th}$ annual conference on computer graphics and interactive techniques, pp. 279-288.*

Pat Hanrahan, Paul Haeberli, "Direct WYSIWYG Painting and Texturing on 3D Shapes", Aug. 1990, ACM, Computer Graphics, vol. 24, Issue 4, pp. 215-223.*

Frederick M. Weinhaus, Venkat Devarajan, "Texture Mapping 3D Models of Real-World Scenes", Dec. 1997, ACM, ACM Computing Surveys, vol. 29, No. 4, pp. 325-365.*

(56) References Cited

OTHER PUBLICATIONS

Robert C. Lansdale, "Texture Mapping and Resampling for Computer Graphics", Jan. 1991, University of Toronto, Thesis.*
Richard B. North, Daniel J. Nigrin, Kim R. Fowler, Richard E. Symanski, Steven Piantadosi, "Automated 'pain drawing' analysis by computer-controlled, patient-interactive neurological stimulation system", 1992, Elsevier Science Publishers, Pain, vol. 50, pp. 51-57.*
Synalink Features, SynaMed Web Page, http://synamed.com/synalinkFeatures.html., Copyright 2010, 2 pgs.
Boston Scientific Corporation, "Boston Scientific Precision Spectra System Programming Manual", Copyright 2010, 580 pgs.

* cited by examiner

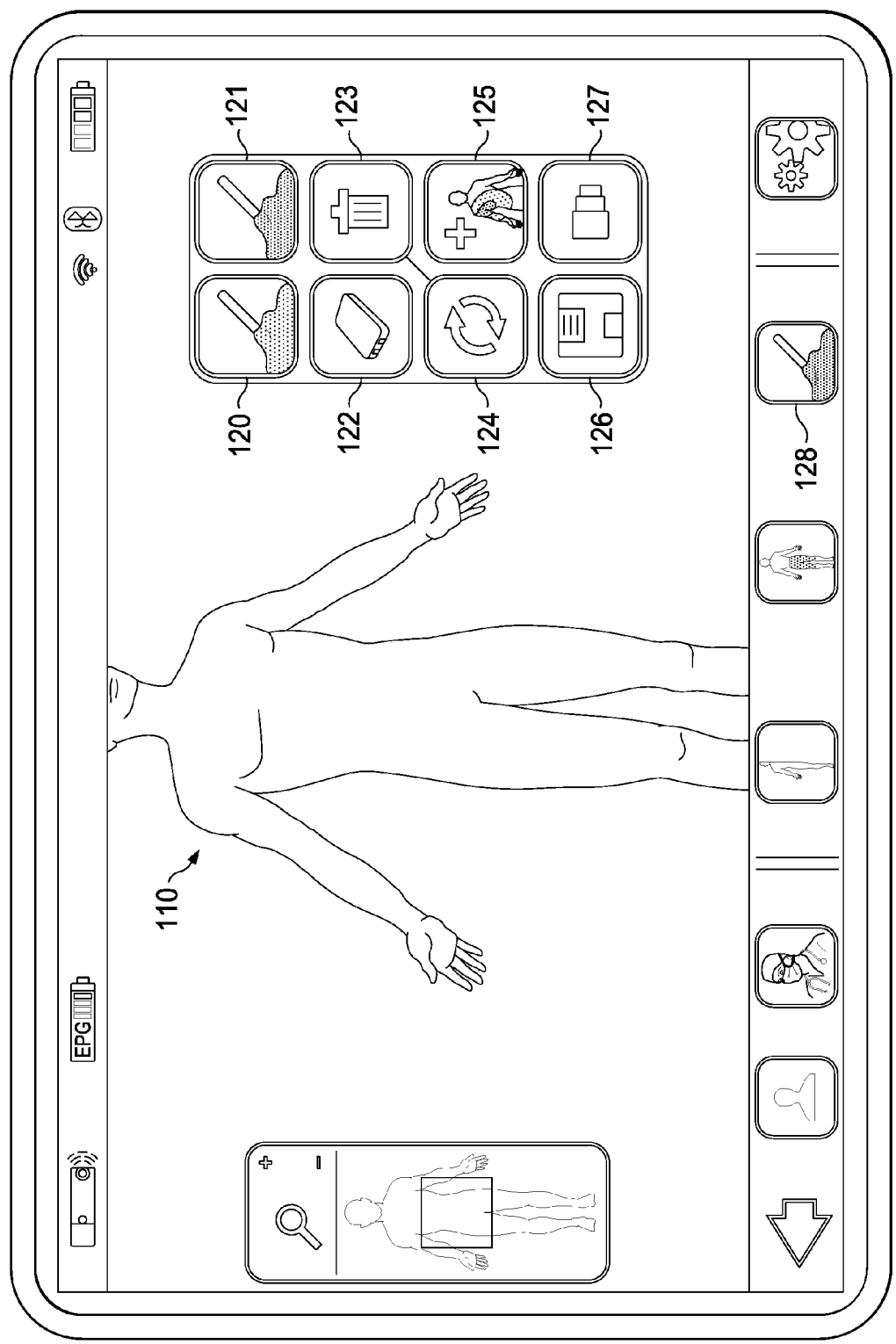

| Public, Jane Q | | PATIENT RECORD ☒ |
|---|---|---|
| Last Name [    ] | | Medical ID # [    ] |
| Middle Init. [    ] | | Patient ID # [    ] |
| First Name [    ] | | Height [    ] |
| Birth Day [ ] [ ] [ ]<br>MM  DD  YYYY | | Weight [    ]<br>Gender [ F ] [ M ] |

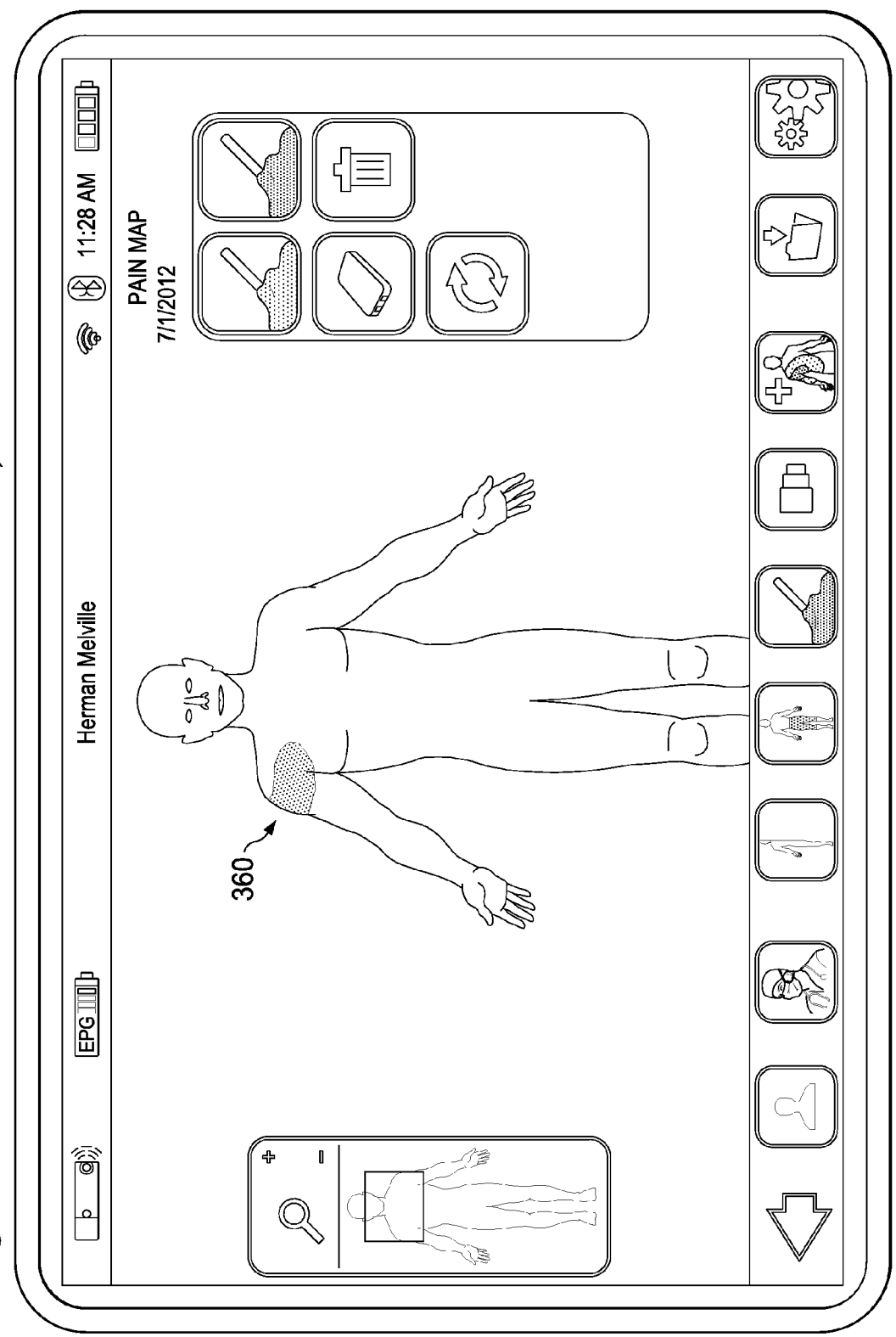

METHOD AND SYSTEM OF PRODUCING 2D REPRESENTATIONS OF 3D PAIN AND STIMULATION MAPS AND IMPLANT MODELS ON A CLINICIAN PROGRAMMER

PRIORITY DATA

The present application is a utility application of provisional U.S. Patent Application No. 61/695,407, filed on Aug. 31, 2012, entitled "Method and System of Producing 2D Representations of 3D Pain and Stimulation Maps and Implant Models on a Clinician Programmer," and a utility application of provisional U.S. Patent Application No. 61/695,721, filed on Aug. 31, 2012, entitled "Method and System of Creating, Displaying, and Comparing Pain and Stimulation Maps," and a utility application of provisional U.S. Patent Application No. 61/695,676, filed on Aug. 31, 2012, entitled "Method and System of Adjusting 3D Models of Patients on a Clinician Programmer," and a utility application of provisional U.S. Patent Application No. 61/824,296, filed on May 16, 2013, entitled "Features and Functionalities of an Advanced Clinician Programmer," the disclosures of each of which are hereby incorporated by reference in their entirety.

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients or restore bodily functions.

Implanted medical devices (for example a neurostimulator) can be controlled using an electronic programming device such as a clinician programmer or a patient programmer. These programmers can be used by medical personnel or the patient to define the particular electrical stimulation therapy to be delivered to a target area of the patient's body, alter one or more parameters of the electrical stimulation therapy, or otherwise conduct communications with a patient. Advances in the medical device field have improved these electronic programmers. For example, some existing programmers allow the creation and display of pain maps and stimulation maps as part of the pain diagnosis and communication with the patient. However, the pain and stimulation maps on existing programmers have certain shortcomings. Among other things, these shortcomings include frequently limitation to two-dimensional displays, imprecise definitions of the pain regions, lack of navigational versatility and flexibility, etc. And to the extent that certain programmers may offer 3D-like displays, these displays are data-intensive and are not conducive for sharing with a remote device, for example another programmer or an external display or remote monitor, such as the secondary display disclosed in U.S. patent application Ser. No. 13/600,875, filed on Aug. 31, 2012, entitled "Clinician Programming System And Method", the disclosure of which is incorporated herein by reference in its entirety.

Therefore, although existing methods and mechanisms for creating and displaying pain maps and stimulation maps have been generally adequate for their intended purposes, they have not been entirely satisfactory in every aspect.

SUMMARY

One aspect of the present disclosure involves an electronic device for visualizing a sensation experienced by a patient. The electronic device includes: a touchscreen display configured to receive a tactile input from a user and display a visual output; a memory storage component configured to store programming code; and a computer processor configured to execute the programming code to perform the following tasks: generating, in response to the tactile input from the user, a three-dimensional (3D) sensation map that represents the sensation experienced by the patient; deriving a two-dimensional (2D) sensation map based on the 3D sensation map, wherein the 2D sensation map contains substantially less data than the 3D sensation map; and sending the 2D sensation map over a network to facilitate a reconstruction of the 3D sensation map using the 2D sensation map.

Another aspect of the present disclosure involves a medical system. The medical system includes: an electronic database; a first portable electronic device that includes: a first electronic processing component configured to produce a two-dimensional (2D) sensation map that is a 2D representation of a three-dimensional (3D) sensation map for a patient, the 2D sensation map containing less data than the 3D sensation map; a first visual display configured to display the 2D sensation map and the 3D sensation map; and a first communications interface configured to send the 2D sensation map to the electronic database; and a second portable electronic device that includes: a second communications interface configured to receive the 2D sensation map from the electronic database; a second electronic processing component configured to reproduce the 3D sensation map based on the 2D sensation map; and a second visual display configured to display the 2D sensation map and the 3D sensation map.

Yet another aspect of the present disclosure involves method of representing a sensation experienced by a patient. The method includes: receiving, from a plurality of predefined three-dimensional (3D) human body models, a selection of a 3D human body model that is customized to the patient based on a set of physical characteristics of the patient; generating, in response to a tactile input from a user, a 3D sensation map that corresponds to the sensation experienced by the patient, wherein the 3D sensation map is generated over the selected 3D human body model; representing the 3D sensation map with a two-dimensional (2D) sensation map, wherein the 2D sensation map contains substantially less data than the 3D sensation map; and facilitating a reconstruction of the 3D sensation map based on the 2D sensation map.

One more aspect of the present disclosure involves a portable electronic apparatus. The portable electronic apparatus includes: means for selecting, from a plurality of predefined three-dimensional (3D) human body models that each have a unique set of physical characteristics including one or more of the following: height, weight, age, gender, and ethnicity, a 3D human body model that most closely match physical characteristics of the patient; means for generating, in response to a tactile input from a user, a first 3D sensation map that indicates a sensation experienced by the patient, wherein the first 3D sensation map is generated over the selected 3D human body model; and means for representing the first 3D sensation map with a first two-dimensional (2D) sensation map, wherein the first 2D sensation map contains substantially less data than the first 3D sensation map; means for sending the first 2D sensation map to a database and receiving a second 2D sensation map from the database; and means for generating a second 3D sensation map based on the second 2D sensation map.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIGS. 2, 3A-3B, 4A-4B, 5A-5B, 6-12 and 19A-19B, 20-23 are graphical user interfaces for generating and displaying pain/stimulation maps according to various aspects of the present disclosure.

DETAILED DESCRIPTION

Figure 1:
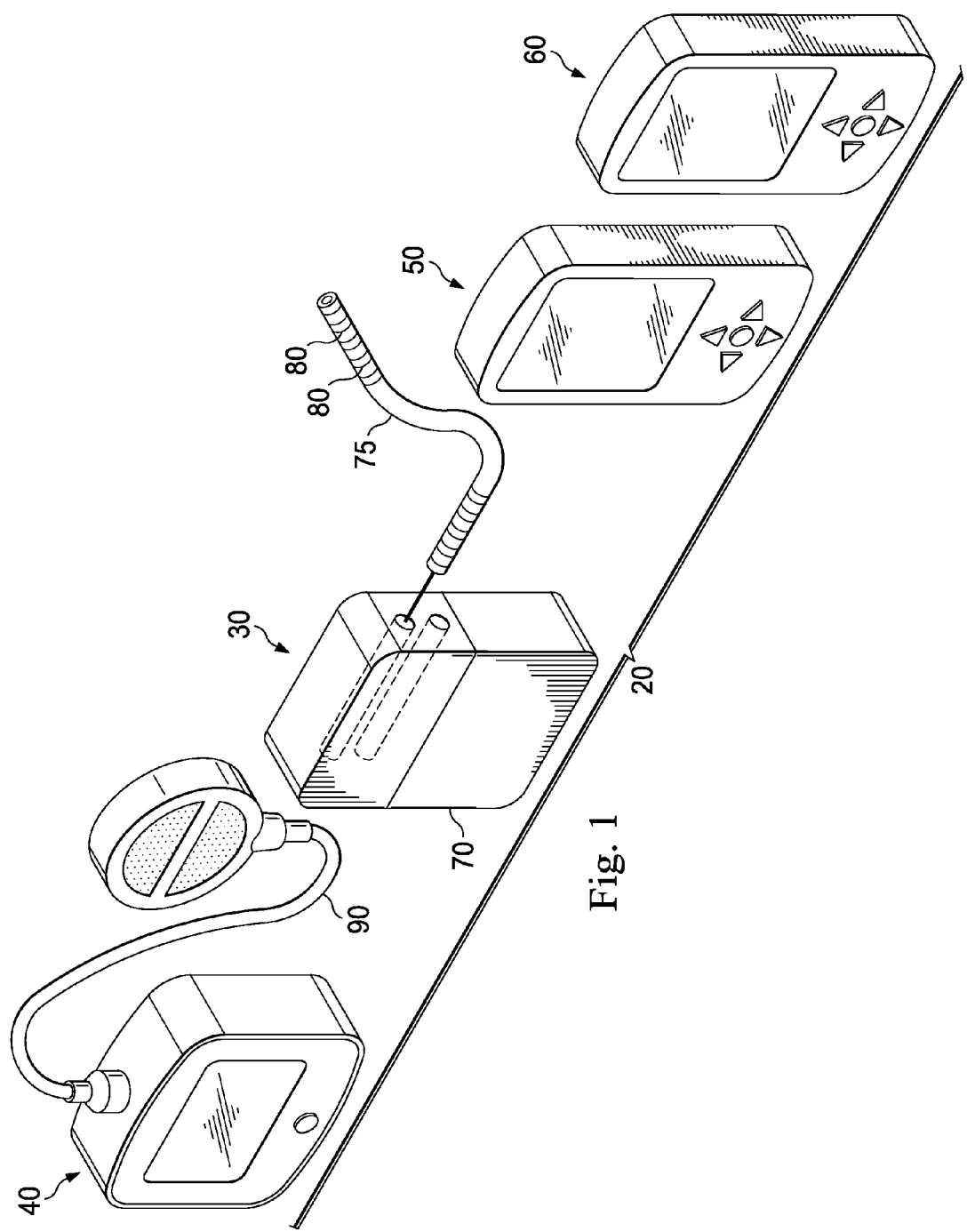
FIG. 1 is a simplified block diagram of an example medical environment in which evaluations of a patient may be conducted according to various aspects of the present disclosure.
Figure 3A:
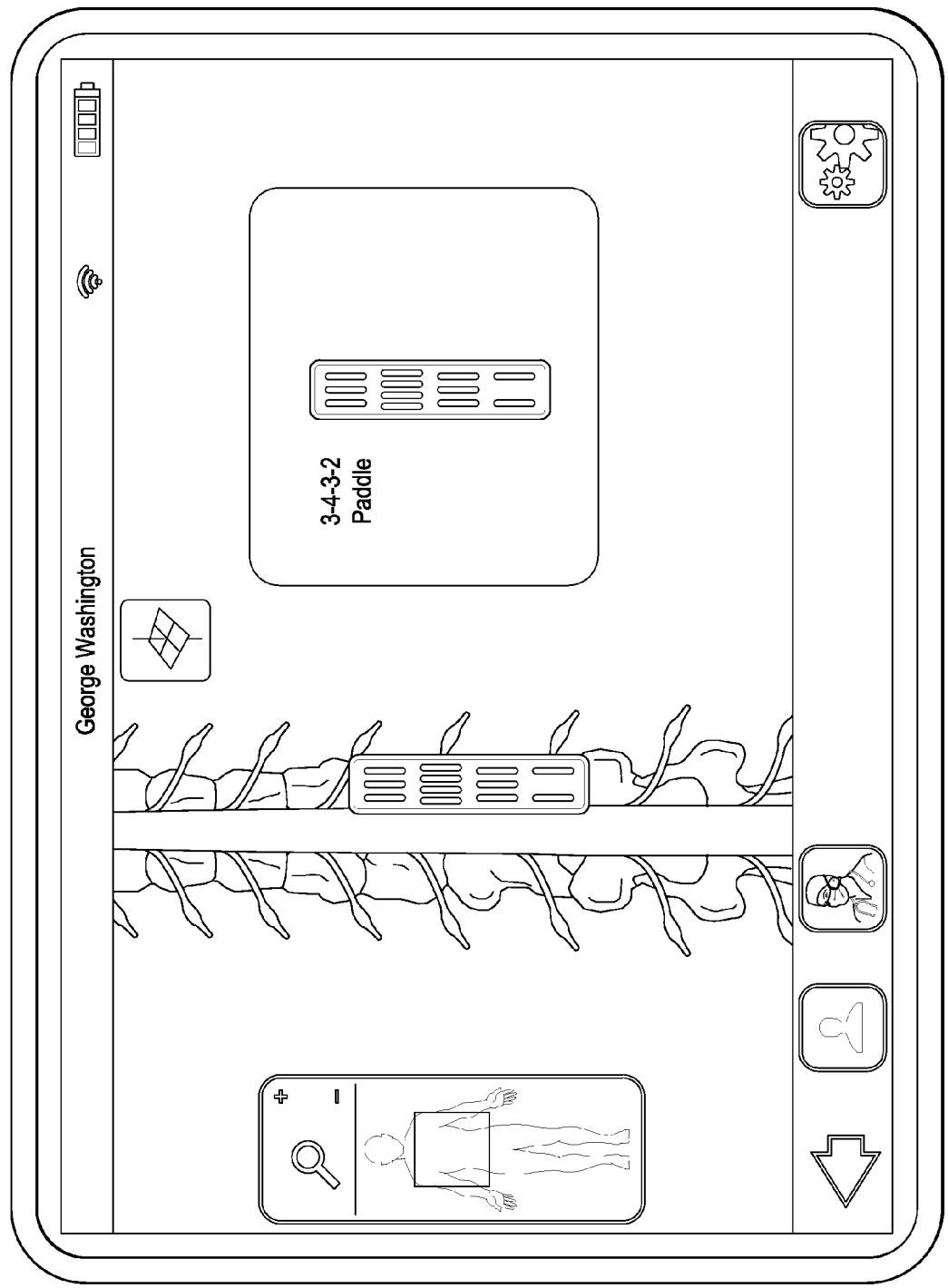
Figure 3B:
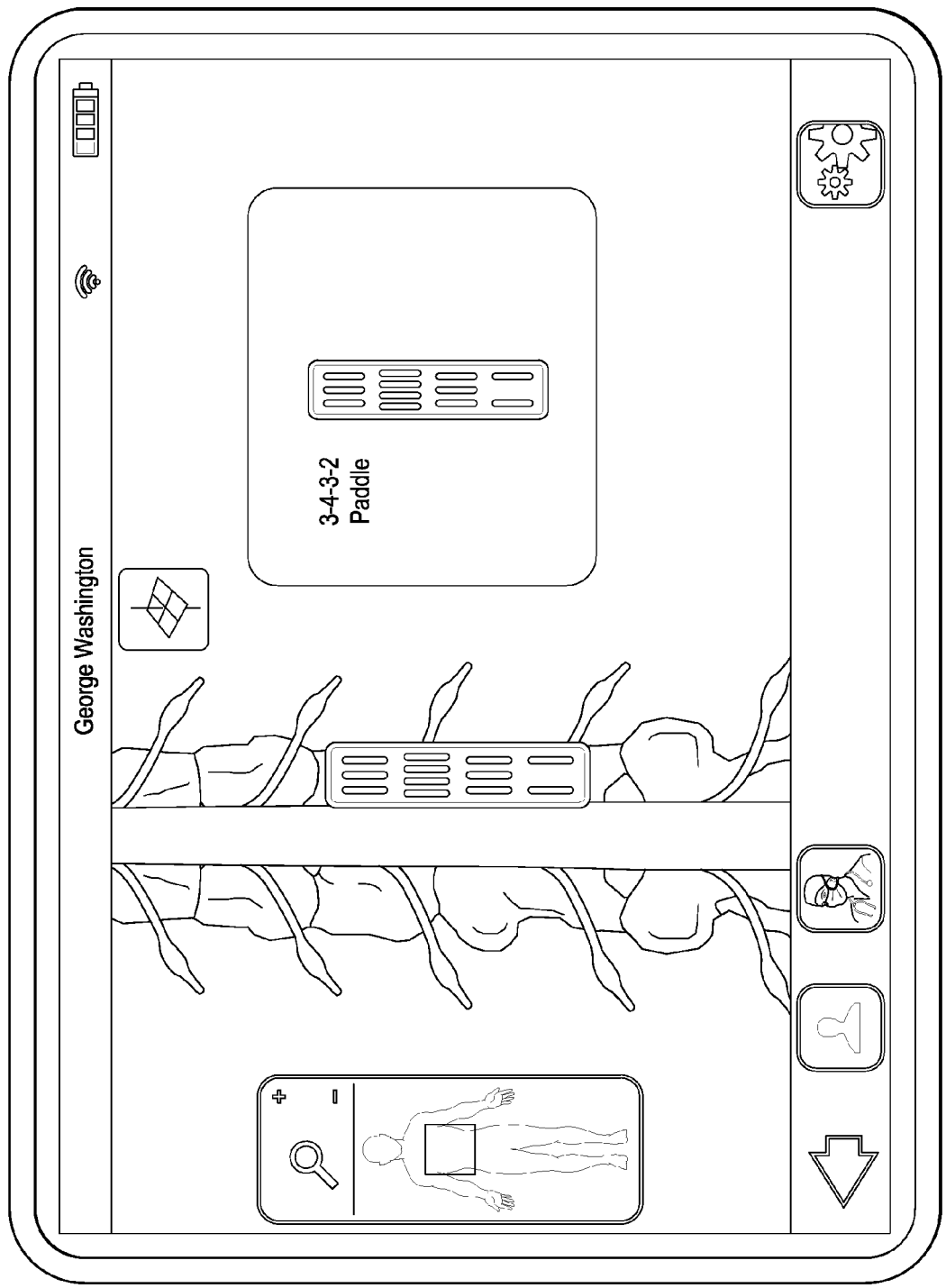

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

In recent years, the use of active implanted medical devices has become increasingly prevalent. Some of these implanted medical devices include neurostimulator devices that are capable of providing pain relief by delivering electrical stimulation to a patient. In that regards, electronic programmers have been used to configure or program these neurostimulators (or other types of suitable active implanted medical devices) so that they can be operated in a certain manner. These electronic programmers include clinician programmers and patient programmers, each of which may be a handheld device. For example, a clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

Over the years, these electronic programmers have achieved significant improvements, for example, improvements in size, power consumption, lifetime, and ease of use. For instance, electronic programmers have been used to generate and/or display pain maps and stimulation maps for a patient. In general, a pain map shows the location or intensity of a patient's pain, and a stimulation map shows the location or intensity of the electrical stimulation (e.g., stimulation delivered by the neurostimulator) perceived by the patient. These pain/stimulation maps can serve as useful tools for diagnosing the patient's pain and treatment and also allow visual/non-verbal communication between a patient and a healthcare professional. In addition, a history of the maps, if collected, can provide a record of a patient's treatment progress, and the maps can also be analyzed across patient groups. In some embodiments, to protect patient privacy, the personal information of the patients is stripped before the history of the pain/stimulation maps are collected and analyzed. In other words, the history of the pain/stimulation maps may be collected and analyzed anonymously in certain embodiments.

Nevertheless, the generation and display of pain/stimulation maps in existing programmers in the medical field may still have drawbacks. Some of these drawbacks include:

Existing pain/stimulation maps are frequently limited to two-dimensional (2D) displays, which do not allow the patient to indicate pain on the side of the body.

Existing pain/stimulation maps do not allow patients to paint the location of their pain. Instead, patients are required to choose a block on the body, which limits the map's precision.

Users (including patients and healthcare professionals) cannot quickly choose a position on the body; they must use arrows to move along or rotate the image.

There is a lack of capability in existing models for comparison and correlation of maps.

Existing pain/stimulation maps may not contain sufficient pain/stimulation history for the patient.

Existing pain/stimulation maps cannot be easily shared.

In addition, to the extent that some programmers may offer the generation and display of certain rudimentary three-dimensional (3D) pain/stimulation maps, these pain/stimulation maps are often quite data intensive. Therefore, the large amount of data associated with these 3D-like pain/stimulation maps makes their storage and transfer very difficult. For example, it is space and time consuming to share some of these 3D-like pain/stimulation maps with a remote server or a remote programmer unit.

To overcome these problems associated with existing electronic programmers discussed above, the present disclosure offers a programmer that allows for the generation and display of versatile and flexible 3D pain maps and stimulation maps. In addition, these pain maps and stimulation maps can be represented in a 2D context so as to make their storage and sharing more convenient and practical.

FIG. 1 is a simplified block diagram of a medical device system 20 is illustrated to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end (referred to as a connection end) of one or more percutaneous, or skin-penetrating, leads. The other end (referred to as a stimulating end) of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer. However, it is understood that the electronic programmer may also be the patient programmer 50 or other touch screen programming devices (such as smart-phones or tablet computers) in other embodiments.

FIGS. 2-12 are example screenshots of a user interface 100 for generating and displaying 3D sensation maps (e.g., pain/stimulations maps) according to the various aspects of the present disclosure. In some embodiments, the user interface 100 may be displayed on a screen of a programmer, for example a capacitive or resistive touch-sensitive display. In other embodiments, the user interface 100 may be displayed on a programmer and an external monitor simultaneously, for example in accordance with U.S. patent application Ser. No. 13/600,875, filed on Aug. 31, 2012, entitled "Clinician Programming System and Method", the disclosure of which is hereby incorporated by reference in its entirety. As such, both the healthcare provider and the patient are able to view the user interface at the same time.

Referring to FIG. 2, the user interface 100A illustrates a 3D model of a human body 110. The 3D human body model 110 includes an entire human body, though the user interface 100 may be configured to view only a portion of the human body model 110 at a time. The human body model 110 can also be moved in all directions, rotated, resized, or otherwise manipulated. In some embodiments, the human body model 110 is customized for a specific patient. For instance, if a patient is tall (e.g., 6 feet or taller), the human body model 110 may be created (or later resized) to be "taller" too, so as to correspond with the patient's height. As another example, if the patient is overweight or underweight, the human body model 110 may be created (or later resized) to be wider or narrower, so as to correspond with the patient's weight. As other examples, if the patient has particularly long or short limbs (or even missing limbs or body parts), hands/feet, or a specific body build, the human body model 110 may be created (or later resized) to correspond with these body characteristics of the patient as well.

In some embodiments, the present disclosure offers a database that includes a plurality of predefined human body models that each correspond to a specific body type, for example a predefined body type for a 40 year old Caucasian male with a height of 6'1 and a weight of 200 pounds, or a 20 year old African American female with a height of 5'5 with a weight of 120 pounds, so on and so forth. In these embodiments, a healthcare professional or the patient can quickly select a predefined body type from this database that most closely matches his/her physical conditions/characteristics. In this manner, the healthcare professional need not spend too much time specifically customizing the human body model 110 to the patient, since a predefined human body model that is substantially similar to the patient is already available from the database. It is also understood that such database may be available to a network of healthcare professionals and may be downloaded to the electronic programmer upon verifying the necessary login credentials. The patient models may also be uploaded from an electronic programmer to the database. In some further embodiments, the clinician programmer discussed herein is configured to capture an image of the patient (for example via an integrated camera). The proportions and other bodily details of the patient may then be automatically adjusted by processing the captured patient image.

FIGS. 3-9 are graphical examples illustrating how a human body model can be customized to more accurately match the physical traits of a patient. FIGS. 3A-3B are graphical illustrations of an implanted medical device (e.g., a paddle lead) relative to a spine of a patient. In FIG. 3A, the patient is a short patient, and therefore the implanted medical device covers more vertebra levels. In comparison, the patient is a tall patient in FIG. 3B, and thus the implanted medical device covers fewer vertebra levels. This is because the spacing between the vertebra levels increase as the patient's height increases, but the length of the implanted medical device will remain the same regardless of the patient's height. Thus, FIGS. 3A-3B highlight the importance of matching the actual patient with a model as closely as possible, as the efficacy of the treatment is dependent on the accurate modeling.

Figure 4A:
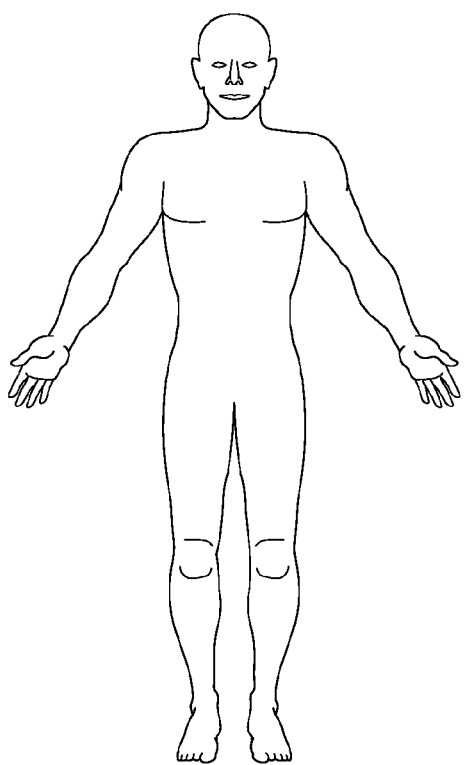
Figure 4B:
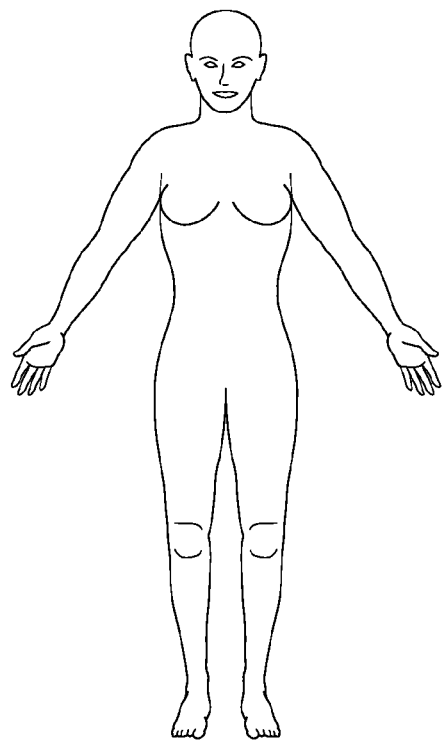
Figure 5A:
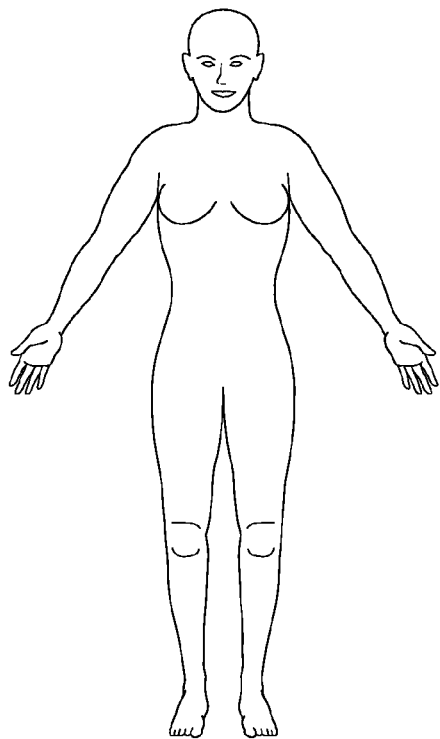
Figure 5B:
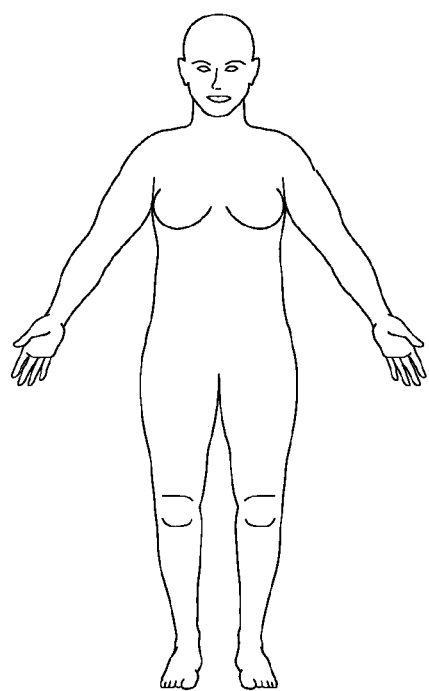
Figures 6, 7:
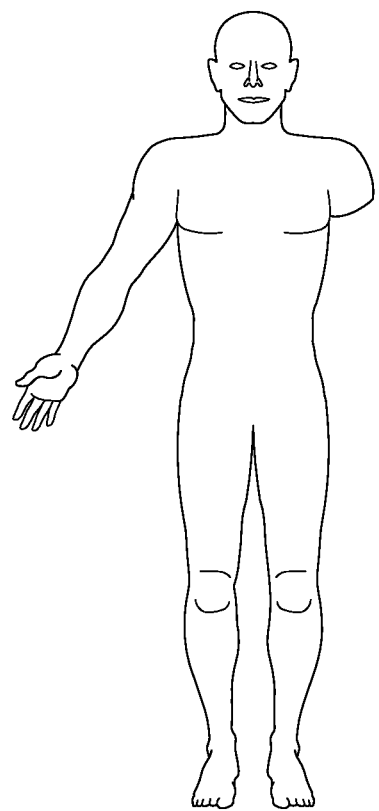
Figure 8:
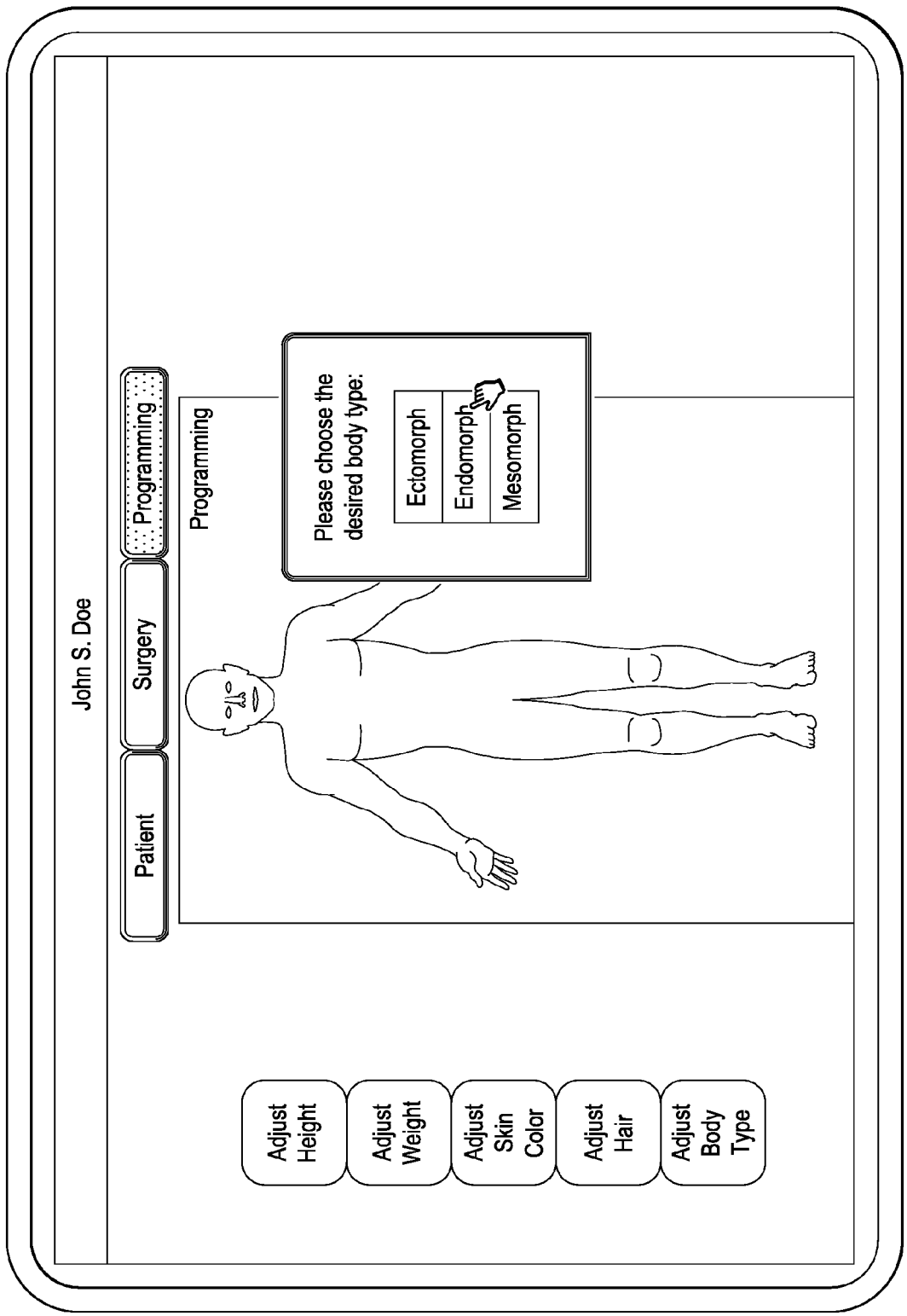

As discussed above, height is not the only variable that can be adjusted in customizing a human body model that closely matches the actual patient. Gender and weight are also among the variables that can be adjusted. As examples, FIG. 4A illustrates a standard male model, FIG. 4B illustrates a standard female model, FIG. 5A illustrates a tall and thin female model, and FIG. 5B illustrates a short and more heavy-set female model. Furthermore, another possible structural adjustment is the removal of appendages, which is illustrated in FIG. 6, where the model is missing a part of his left arm. The removal of appendages may be accomplished by not using all the vertices of the original model, for example. And although not specifically shown for reasons of simplicity, other variables that can be adjusted include skin color, hair color, eye color, etc.

Figure 9:
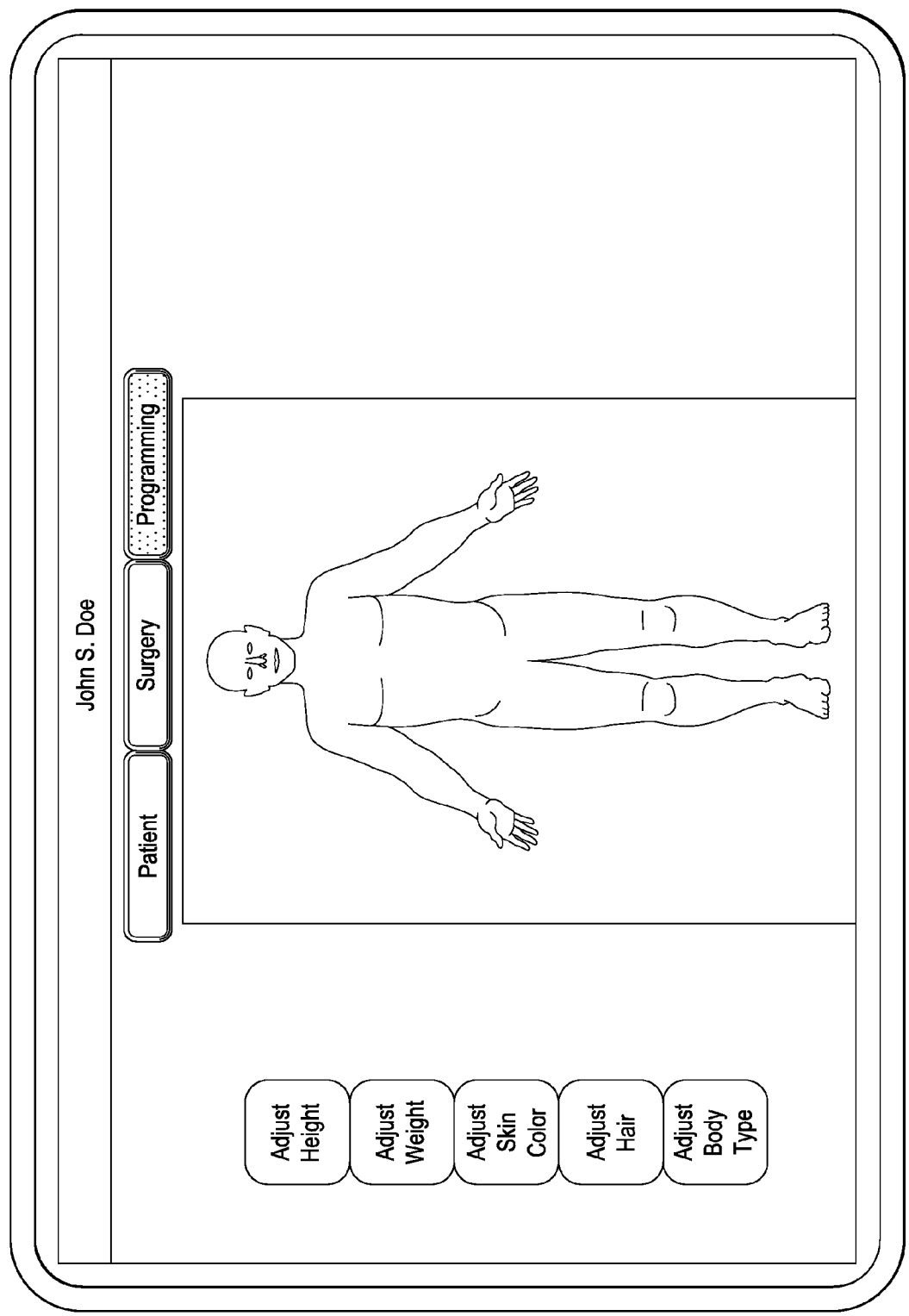

FIG. 7 is an example patient information record in which the user (who may or may not be the patient) may enter patient specifics such as height, weight, gender, body type, etc. discussed above. In some embodiments, the patient record may be used to automatically modify the human body model representing the actual patient. In other embodiments, the user may manually adjust the human body model manually. In yet other embodiments, the user may make manual adjustments to the human body model after a human body model has been automatically generated based on the patient information entered into the patient record. For example, in FIG. 8, a standard male model has been generated for patient "John S. Doe" based on the data entered into his patient record. The user wants to make further manual adjustments to the automatically-generated model, and thus a list of modification options appears, which includes "Adjust Height," "Adjust Weight," "Adjust Skin Color," "Adjust Hair," and "Adjust Body Type." The user wishes to make an adjustment to the body type and selects the option "Adjust Body Type." As a result, a list of body type options appears, which includes "Ectomorph" (heavy/rounded), "Endomorph" (lean), and "mesomorph" (muscular). Referring now to FIG. 9, an adjusted model is shown as a result of the user selecting "Ectomorph." Thus, the model is FIG. 9 is heavier and more rounded compared to the model in FIG. 8 before the adjustment. Of course, these adjustment options discussed above are merely examples, and additional adjustment options are envisioned in other embodiments.

Referring now back to FIG. 2, the user interface 100 also displays a plurality of menu items 120-127 to assist with the generation and display of the pain maps and stimulation maps (not visible in FIG. 2). The display of the menu items 120-127 is triggered by the user pressing on a virtual button 128. In the illustrated embodiment, the menu item 120 is used to generate a pain map or a stimulation map. After selecting the menu item 120, the patient can user his/her finger(s) as a simulated brush to draw or paint an area on the human body model 110 that corresponds to a region of pain the patient experiences. For example, if the patient feels pain in his/her shoulder, he/she can paint a pain map on the shoulder region of the human body model 110. The human body model 110 can also be rotated, so that the patient can paint the pain map in different regions of the human body model. The patient may revise the pain map to correspond as closely with the actual perceived regions of pain as possible. To facilitate the painting/drawing of the pain maps, the simulated brush may be of adjustable size.

The stimulation map may be created in a similar manner, except that the stimulation map corresponds with the perceived stimulation experienced by the patient. The pain map and stimulation map are drawn on a touch-sensitive screen in the illustrated embodiment. A graphics accelerator may be used to speed up the generation of these maps.

Once the virtual button 128 is engaged to trigger the display of the menu items 120-127, the menu items 120-121 may be used to indicate different levels of intensity of the pain or stimulation. For example, referring to FIG. 10, after the menu item 120 is used to create a "baseline" pain map that covers a region of the body in general, the menu item 121 (shown in FIG. 2) may be used to indicate a region where the pain is more intense. In the embodiment of the user interface 100B shown in FIG. 10, the patient may draw a region 140 as a "baseline" pain region to indicate general pain. This region 140 may represent the body regions where the patient feels some degree of pain. The patient may also draw a region 142 within the region 142 as an "intense" or "acute" pain region. In other words, the patient may feel much more pain in the region 142 than in the rest of the region 140. The degree of the pain intensity may correspond with a color (or hue) of the region, and a variety of colors may be available to represent different degrees of pain. Thus, a pain map of the present disclosure may reveal various regions with different degrees of pain. In some embodiments, the more painful regions are represented by darker colors, and the less painful regions are represented by lighter colors. The opposite may be true in other embodiments. In further embodiments, various pain maps may be created to represent different types of pain, for example a numbness, a burning pain, a tingling, a soreness, etc. These different types of pain may be represented by pain maps with different colors or different textures, for example. In yet other embodiments, the depth of pain (whether the pain is only skin-deep or penetrates to the muscle level) may also be represented by the pain maps, for example by different colors or different textures of the pain maps. It is also understood that the pain/stimulation maps may be resized proportionally to automatically correspond with the underlying human body model. That is, if the human body model on which the pain/stimulation maps are resized, the pain/stimulation maps may be resized accordingly.

Figure 10:
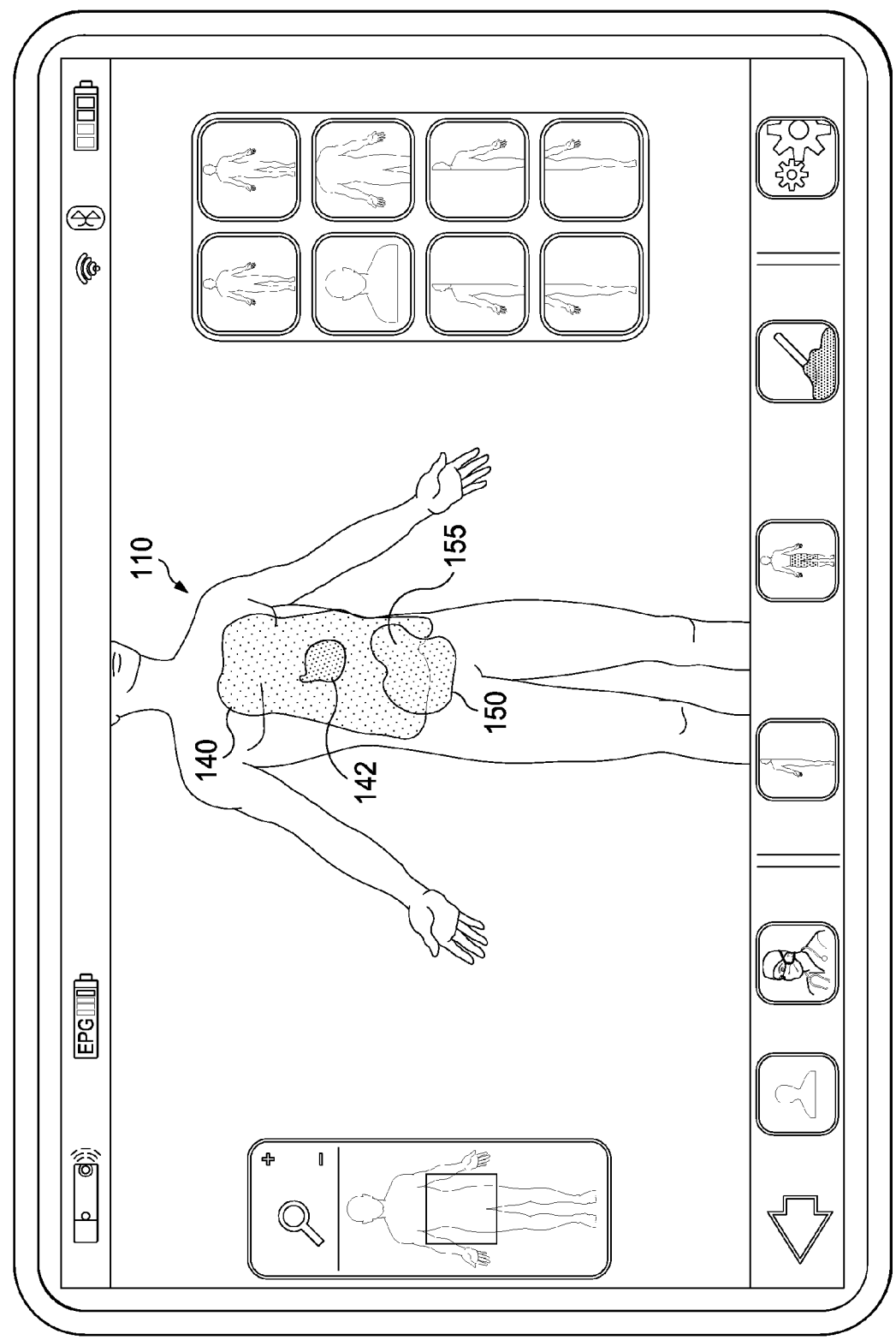

Similarly, the patient may also draw a region 150 to indicate a region on the body where the patient experiences stimulation while the stimulation therapy is active. The stimulation maps may be configured in a similar manner as the pain maps. In other words, the stimulation maps may be configured to portray different intensities of stimulation sensations, different regions of stimulation sensations, different types of stimulation sensations or different depths of stimulation sensations. Note that the pain region 140 and the stimulation region 150 may be displayed individually, or simultaneously, as shown in FIG. 10. An overlapping region 155 (an overlapping between the pain region 140 and the stimulation region 150) may also be displayed, which is helpful in helping the healthcare professional in diagnosing and treating the patient.

It is understood that although pain maps are used as an example herein for illustration purposes, stimulation maps containing regions with different stimulation intensity may be generated in the same manner.

Referring back to FIG. 2, the menu item 122 is used to erase or remove portions of the pain map or the stimulation map. This is done when the patient needs to revise an existing pain map or stimulation map, for example when the pain map or stimulation map is dated and no longer accurately reflects the patient's perceived pain or stimulation.

The menu item 123 is used to delete an existing pain map or stimulation map.

The menu item 124 is used to cycle through different maps, such as switching between pain maps and stimulation maps.

The menu item 125 is used to generate a new pain map or a new stimulation map (or updated versions of existing pain/stimulation maps).

The menu item 126 is used to save changes to a pain map or a stimulation map.

The menu item 127 is used to play back a migration of pain maps and stimulation maps, or a combination thereof. The migration of the pain maps and stimulation maps may be historical (i.e., in the past) or projected (i.e., in the future). Among other things, this may be used to show progression of treatment.

Of course, these menu items 120-127 are merely examples. Some of these menu items may be removed, and other menu items may be added in alternative embodiments to carry out the generation and editing of the pain map and stimulation map.

The present disclosure also allows for predefined pain or stimulation regions. For example, referring now to FIG. 11, the user interface 100C shows a plurality of menu items 160-167 that each correspond to a predefined pain or stimulation region on the human body model 110. For example, in the embodiment shown, the menu item 160 may correspond to a predefined pain region in the right arm of the patient; the menu item 161 may correspond to a predefined pain region in the left arm of the patient; the menu item 162 may correspond to a predefined pain region in the waist and thighs of the patient; the menu item 163 may correspond to a predefined pain region in the abdomen of the patient; the menu item 164 may correspond to a predefined pain region in the right lower leg of the patient; the menu item 165 may correspond to a predefined pain region in the lower left leg of the patient; the menu item 166 may correspond to a predefined pain region in the right foot of the patient; and the menu item 167 may correspond to a predefined pain region in the left foot of the patient. In certain embodiments, the severity or intensity of pain/stimulation, type of pain/stimulation, and depth of pain/stimulation may be selected as a part of the predefined regions.

Figure 11:
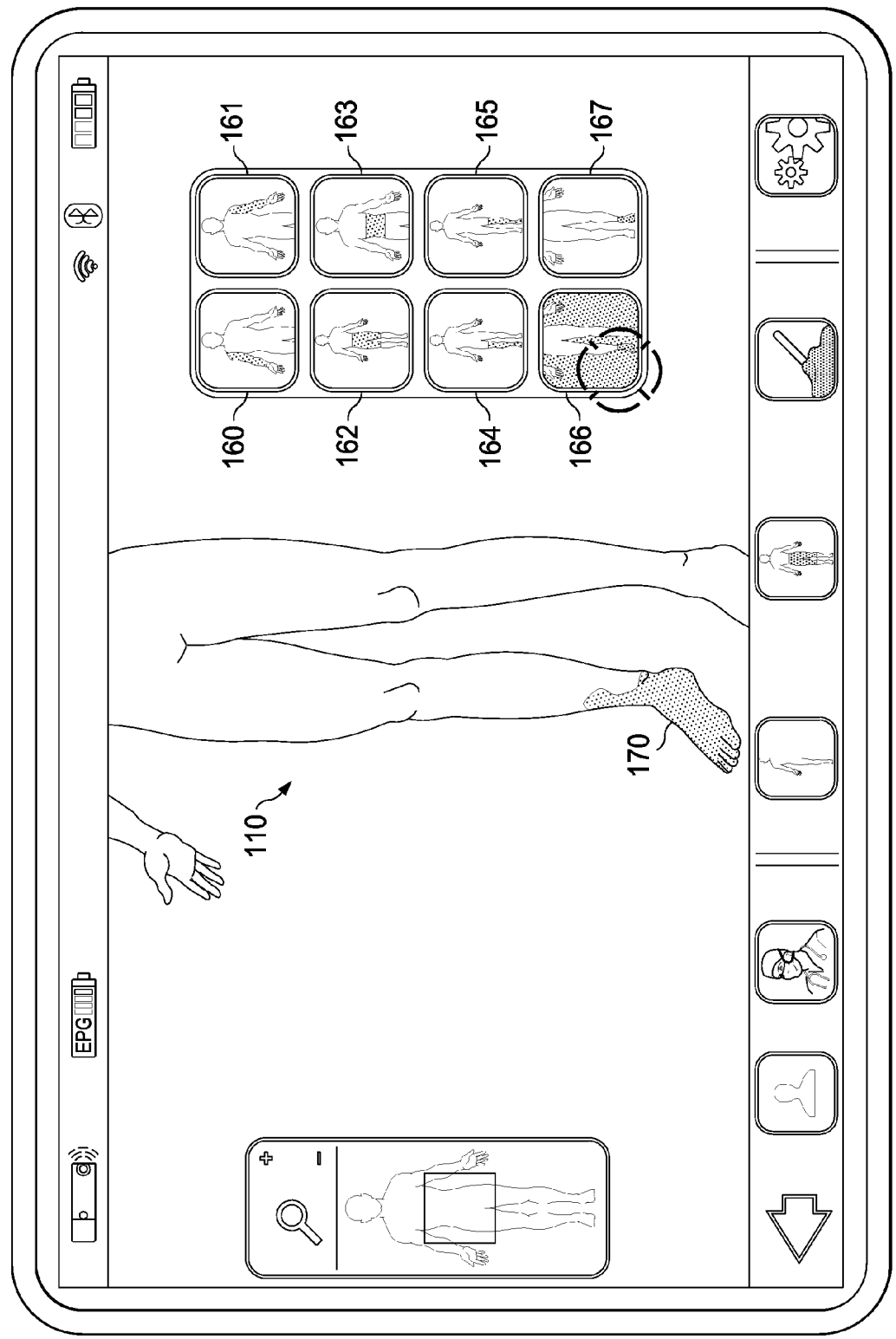
Figure 12:
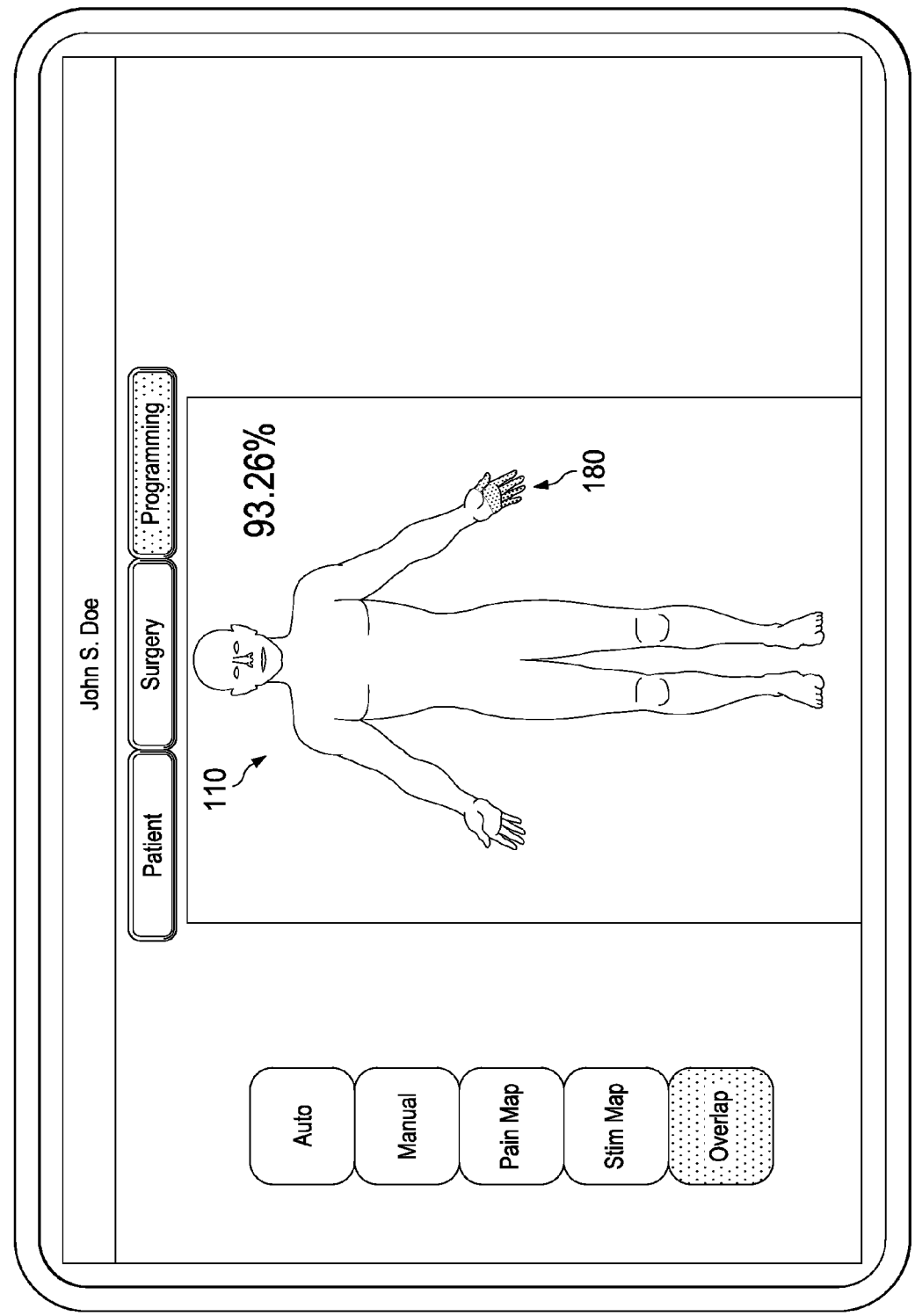

In the embodiment shown in FIG. 11, the menu item 166 is selected, which automatically generates a pain region 170 that covers the right foot of the human body model 110. The pain region 170 can then be revised by the patient to create a pain map that more accurately matches with the pain experienced by the patient. In the same manner, a predefined stimulation region may be automatically generated and then revised to create a desired stimulation map.

The correlations between stimulation parameters (e.g., milliamps, polarity, pulse width, frequency, lead position) or activity parameters (e.g., sitting, standing, sleeping, running, etc.) and perceived stimulation maps are a valuable part of map analysis, because they indicate the degree to which a parameter is related to a certain effect. Map correlations, which can be carried out between individual stimulation programs ("programs") and effective or perceived stimulation maps, are also possible between groups of programs ("programs sets") and an effective stimulation map. A more detailed discussion of stimulation parameters, programs and program sets is found in U.S. patent application Ser. No. 13/601,631, filed on Aug. 31, 2012, and entitled "Programming and Virtual Reality Representation of Stimulation Parameter Groups" to Norbert Kaula, et al., the content of which are hereby incorporated by reference in its entirety. Note that in some embodiments, the "program sets" may also be referred to as "programs" while the "programs" may be referred to as "sub-programs."

The present disclosure further allows for a determination of an overlap between a pain map and a stimulation map. For example, referring now to FIG. 12, after a pain map and a stimulation map have been generated, the user interface 100D can be used to determine an overlap 180 between the pain map and the stimulation map. The overlap may vary as a percentage from 0% to 100%. In some embodiments, or even greater than 100% in other embodiments. For example, if the pain map covers an abdominal region, and the stimulation map covers the abdominal region as well as a chest region, then the overlap may be considered to be greater than 100%. It may be desirable to have a close match between the pain map and the stimulation map, as that may indicate an optimal and efficient stimulation of the pain regions for the patient. For purposes of providing an example, the overlap between the pain and stimulation maps is computed to be at 93.26% in the embodiment shown. In addition, the pain and stimulation maps may be weighted differently, for example by using a slider tool (not illustrated herein), with a readout of the weights. There may be two different types of weights. One weight is to use the slider tool to visually indicate the differences between the pain areas and the stimulation areas. The slider tool may be used to fade in and out of the two types of maps (i.e., pain map and stimulation map) while they are overlapped. The region of overlap may be represented by a different color from either of the maps. Another weight is to show areas of the model that are more important for pain management. In addition, the user interface may also indicate areas of stimulation that are not overlapping a pain area. Such areas of stimulation are unnecessary and may cause discomfort for the patient. In some embodiments, the "extra" stimulation areas are shown on the map and may also be accompanied by a "+" sign next to the percentage. Alternatively, the user interface may be configured to only display areas of pain and/or stimulation that are outside the overlapped area between pain map and stimulation map. The degree of non-overlapped areas may also be indicated by a percentage number.

In various embodiments, any of the maps in Table 1 below may be compared, either one to another, or in combinations. The possibilities range from maps recorded at the initial session through the current session, and include pain maps (PAIN); stimulation program maps (STIM-Px), where x may vary up to a predetermined number (e.g. 4); and stimulation program set maps (STIM-Sx), where y is determined by the number of programs (x).

For example, if there are three stimulation programs (STIM-P1, STIM-P2, STIM-P3), then there are seven possible stimulation program sets (STIM-P1, STIM-P2, STIM-P3, STIM-P1+STIM-P2, STIM-P1+STIM-P3, STIM-P2+STIM-P3, STIM-P1+STIM-P2+STIM-P3).

TABLE 1

Map List

| $PAIN_{init}$ | ... | $PAIN_{curr}$ |
| $STIM\text{-}Px_{init}$* | ... | $STIM\text{-}Px_{curr}$ |
| $STIM\text{-}Sy_{init}$* | ... | $STIM\text{-}Sy_{curr}$ |

*Each stimulation category includes subcategories corresponding to stimulation and the activity parameters discussed above.

FIGS. 13-18 are flowcharts of various methods of generating and manipulating the pain and stimulation maps according to the various aspects of the present disclosure. It is understood that the flowcharts shown in FIG. 13-18 have been simplified for a better understanding of the inventive concepts of the present disclosure. Accordingly, it should be noted that additional processes may be provided before, during, and after the methods of FIGS. 13-18, and that some other processes may only be briefly described herein.

Figure 13:
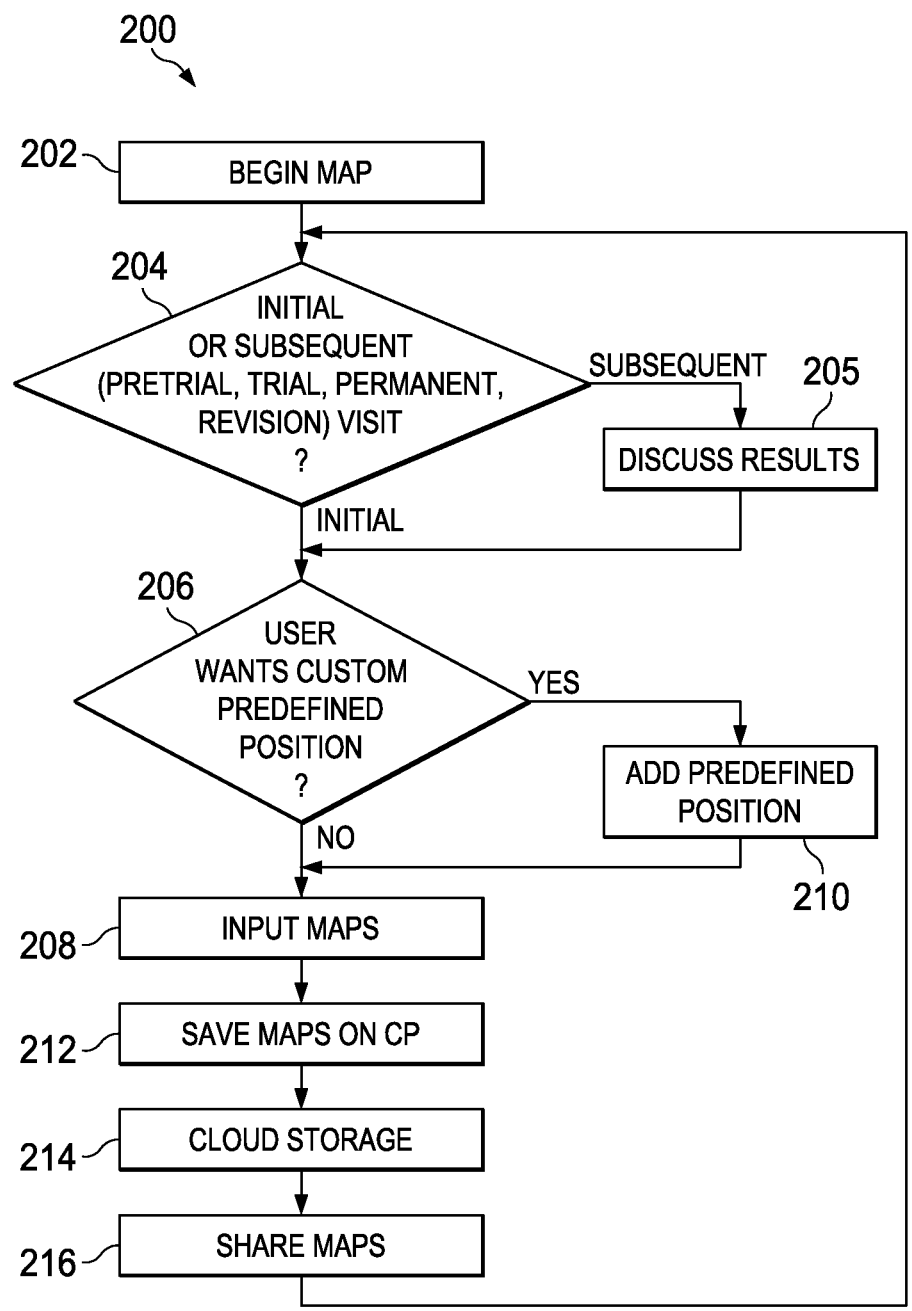
FIGS. 13-18 and 24-27 are flowcharts illustrating example process flows for generating and displaying pain/stimulation maps according to various aspects of the present disclosure.

Referring to FIG. 13, a method 200 describes an overview of the mapping process (with respect to pain or stimulation) and the utilization of the maps according to the various aspects of the present disclosure. The method 200 includes a step 202 to begin a mapping process. The method 200 continues with a decision step 204 to determine whether it is the patient's initial visit with the healthcare professional or a subsequent visit, which may include pretrial visits, trial visits, or permanent revision visits. If it is a subsequent visit for the patient, the method 200 proceeds with a step 205, in which a healthcare professional may discuss results with the patient. The method 200 may then proceed to a decision step

206 to determine whether the user (e.g., patient or healthcare professional) wants custom predefined regions/positions for the map generation, for example in accordance with the discussions above with reference to FIG. 11.

However, if it is the patient's initial visit, the method 200 proceeds to the step 206 directly. If the user does not want the custom predefined regions/positions, the method 200 proceeds to a step 208 from the decision step 206, in which the patient draws or paints the pain and/or stimulation maps on the electronic programmer, for example in accordance with the discussions above with reference to FIG. 2-12. However, if the user does want to use the custom predefined regions/positions, the method 200 proceeds to a step 210 from the decision step 206, in which the user may select a predefined pain/stimulation region from a list of available ones. The patient may then use that predefined pain/stimulation region as a starting map and generate the desired pain/stimulation map by revising the starting map.

After the pain/stimulation map has been generated, the method 200 proceeds with a step 212 to save the pain/stimulation map on the programmer, for example the clinician programmer. The method 200 then continues with a step 214, in which the saved map is sent to a cloud storage, which may include one or more remote electronic databases. Thereafter, the method 200 proceeds with a step 216, in which the maps are shared, for example with another remotely located clinician programmer via suitable means of telecommunication. The method 200 may then loops back to the decision step 204 and repeats the various steps discussed above.

Figure 14:
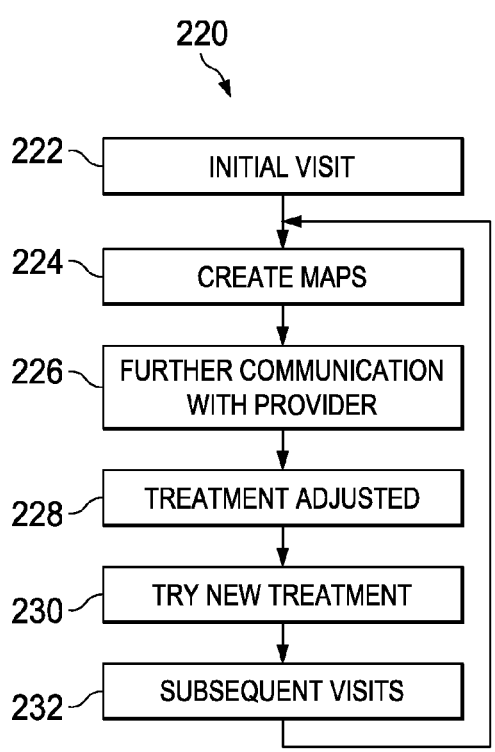

Referring now to FIG. 14, a method 220 describes a patient experience with the pain/stimulation map generation according to the various aspects of the present disclosure. The method 220 begins with a step 222, in which the patient makes an initial visit with a healthcare professional. The method 220 continues with a step 224, in which the patient creates pain/stimulation maps using an electronic programmer, for example in accordance with the discussions above with reference to FIG. 2-12. The method 220 continues with a step 226, in which the patient may further communicative with the healthcare provider regarding the pain or stimulation the patient is experiencing, and whether the pain or stimulation maps are accurate. The method 220 then proceeds to step 228, in which the treatment (e.g., stimulation therapy) is adjusted for the patient based on the feedback from the patient received from the step 226. Thereafter, a new treatment may be delivered to the patient in step 230. The steps 224-230 may represent a typical visit for the patient. The method 220 further includes a step 232, in which the patient makes one or more subsequent visits with the healthcare provider, and the steps 224-230 may be repeated for those subsequent visits.

Figure 15:
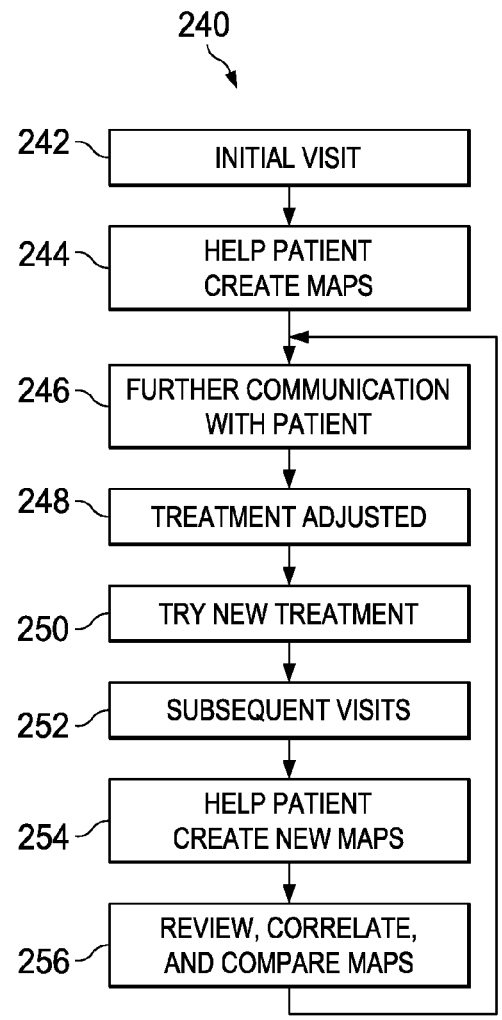

Referring now to FIG. 15, a method 240 describes a healthcare provider experience with the pain/stimulation map generation according to the various aspects of the present disclosure. The method 240 begins with a step 242, in which a patient makes an initial visit with the healthcare provider. The method 240 continues with a step 244, in which the healthcare provider helps the patient create the pain/stimulation maps using the electronic programmer, for example in accordance with the discussions above with reference to FIG. 2-12. The method 240 continues with a step 246, in which the healthcare provider further communicates with the patient regarding the pain or stimulation the patient is experiencing, and whether the pain or stimulation maps are accurate. The method 240 then proceeds to step 248, in which the treatment (e.g., stimulation therapy) is adjusted for the patient based on the feedback from the patient received from the step 246. Thereafter, a new treatment may be delivered to the patient in step 250.

The steps 244-250 may represent a typical visit between the patient and the healthcare provider. The method 240 may further include a step 252, in which the healthcare provider receives one or more subsequent visits from the patient. In that case, the method 240 proceeds to step 254, in which the healthcare provider helps the patient create new pain/stimulation maps. The method 240 then continues with step 256, in which the healthcare provider uses the electronic programmer to review, correlate, and compare the various pain/stimulation maps created from each patient visit. This helps the healthcare provider diagnose the progression of the pain and the evaluate effectiveness of the various treatment programs and may be used to predict potential revision surgery. The method 240 may loop back to step 246 and repeat the steps thereafter when necessary.

Figure 16:
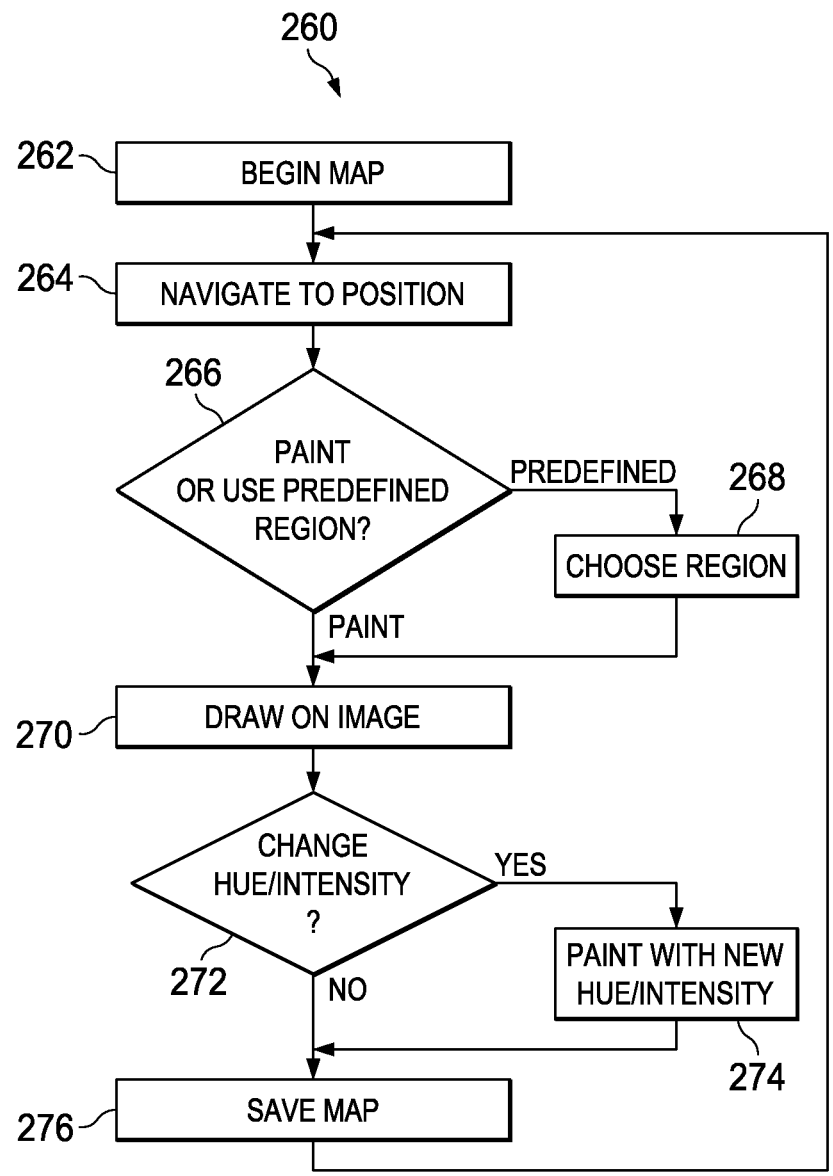

Referring now to FIG. 16, a method 260 describes a pain/stimulation map input process according to the various aspects of the present disclosure. The method 260 begins with a step 262, in which a pain/stimulation map generation process is initiated. The method 260 continues with step 264, in which the patient navigates to a general location of the 3D human body model where he/she would like to paint a pain/stimulation map. The method 260 proceeds with a decision step 266 to determine whether a predefined pain/stimulation region should be used, or whether the generation of the pain/stimulation map should be manual. If the patient wishes to use a predefined pain/stimulation region, for example in accordance with the discussions above with reference to FIG. 11, the method 260 proceeds to a step 268 from the step 266, in which the patient is prompted to choose a target predefined pain/stimulation region from a list of available ones. On the other hand, if the patient wishes to manually generate a pain/stimulation map, the method 260 proceeds to step 270 from the step 266, in which the patient draws or paints the pain/stimulation map on the 3D human body model, for example in accordance with the discussions above with reference to FIG. 2. The method 260 then proceeds to another decision step 272 to determine if the patient wishes to change the hue/intensity of the pain/stimulation map. If the answer is yes, then the method 260 continues with a step 274, in which the patient paints on the pain/stimulation map with new hue/intensity. On the other hand, if the answer from the decision step 272 is no, then the method 260 continues with a step 276, in which the pain/stimulation map generation is tentatively complete, and the generated pain/stimulation map may be saved. If additional work needs to be done to the pain/stimulation map, the method 260 may loop back to the step 264 and may repeat the steps 266-276 again.

Figure 17:
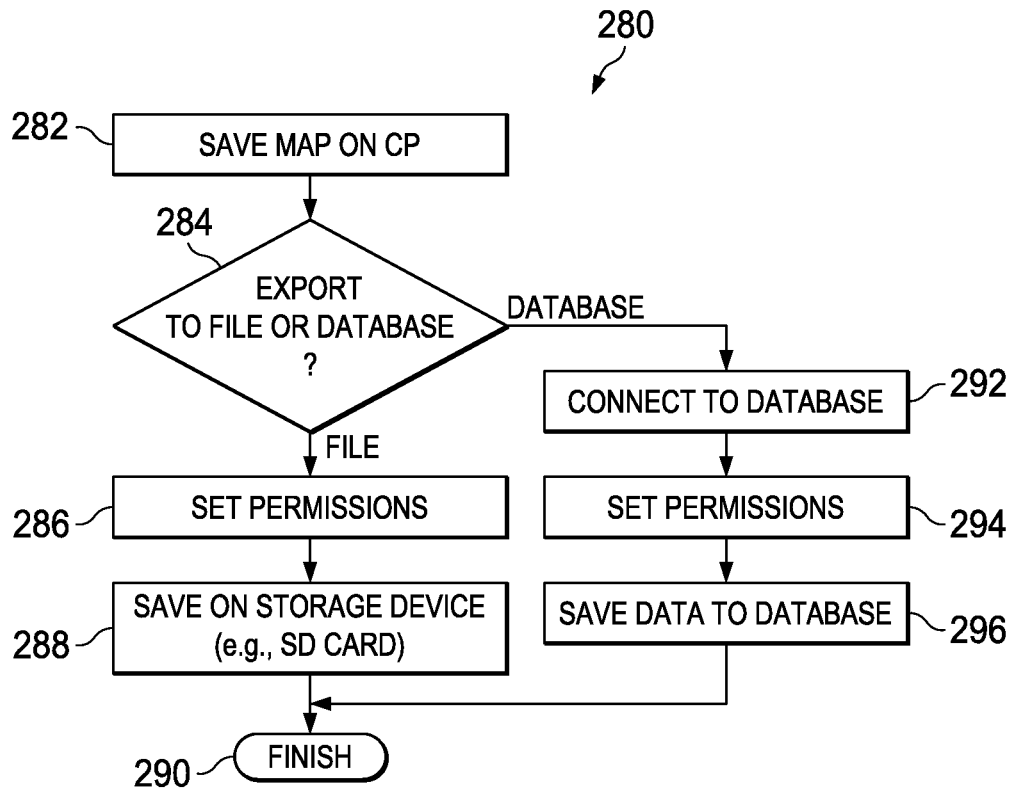

Referring now to FIG. 17, a method 280 describes a transmission process of the pain/stimulation map according to the various aspects of the present disclosure. The method 280 begins with a step 282, in which the pain/stimulation map generated by the patient (with the help from the healthcare provider) is saved on the electronic programmer (e.g., the clinician programmer). The method 280 continues with a decision step 284 to determine whether the pain/stimulation map should be exported to a file, or to a database, or even to a printout/report. In the answer from the decision step 284 is that the pain/stimulation map should be exported to a file, then the method 280 proceeds to a step 286 to set permissions on who (e.g., what users) can view the pain/stimulation maps and/or what restrictions (if any) are placed on the pain/stimulation maps. Thereafter, the method

280 continues to a step 288 to save the pain/stimulation map as a file on a storage device. The storage device includes a local (though not necessarily integrated into the programmer itself) storage device, for example an SD card or a hard drive. The method 280 then finishes at step 290.

However, if the answer from the decision step 284 is that the pain/stimulation map should be exported to a database, the method 280 will proceed to a step 292 to establish a connection with the database. The database may be a remotely located electronic database that is telecommunicatively coupled to the electronic programmer through a wired or wireless network. The method 280 then continues with a step 294 to set permissions as to who may retrieve and view the pain/stimulation maps from the database and/or what restrictions (if any) are placed on the pain/stimulation maps. The method 280 then continues to a step 296 to actually save the pain/stimulation map to the database. Thereafter, when necessary (and with the appropriate permissions), the pain/stimulation maps may be downloaded to another electronic programmer from the database.

Figure 18:
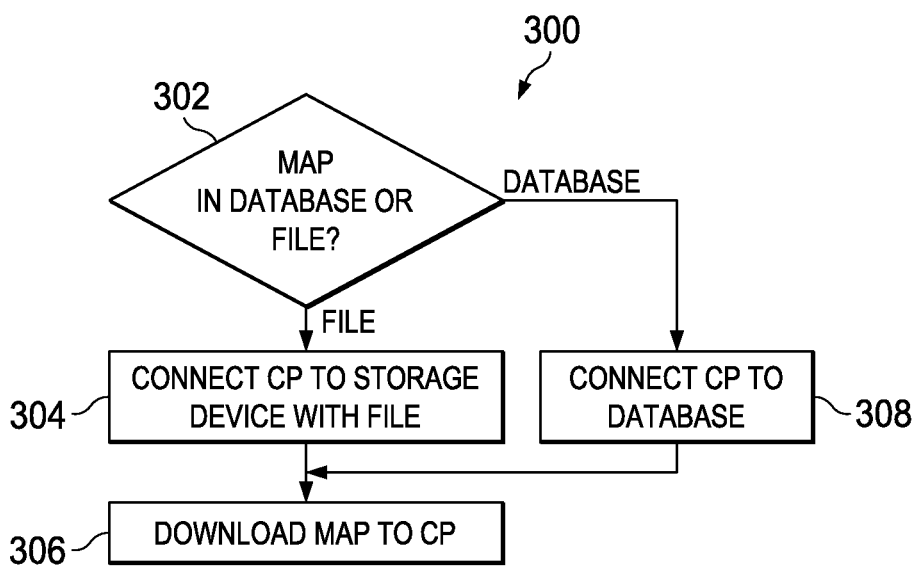

Referring now to FIG. 18, a method 300 describes a reception process of the pain/stimulation map according to the various aspects of the present disclosure. Before the method 300 is performed, it is understood that the pain/stimulation to be received has already been uploaded to and saved in a database or in a local storage device, for example as discussed above with reference to FIG. 17. The method 300 begins with a decision step 302 to determine whether the pain/stimulation map has been saved as a file in a local storage device or uploaded to a remote database. If the answer from the decision step 302 is that the pain/stimulation map has been saved as a file in a local storage device, the method 300 proceeds to a step 304 to connect the programmer to the storage device in which the file is stored. The file (containing information regarding the pain/stimulation map) may then be downloaded to the target programmer in a step 306. The pain/stimulation map may then be viewed on the target programmer. On the other hand, if the answer from the decision step 302 is that the pain/stimulation map has been saved to a remote database, the method 300 proceeds to a step 308 to connect the programmer to the database in which the file is stored. The file (containing information regarding the pain/stimulation map) may then be downloaded to the target programmer in the step 306 again.

The discussions above describe how a pain map or a stimulation map can be generated on a 3D human body model. Thus, the pain/stimulation map discussed above may be referred to as 3D pain/stimulation maps. The 3D pain/stimulation maps allows a patient to accurately portray the pain and stimulation experienced by the patient, and they also allow the healthcare professional to better diagnose the pain and to develop a suitable treatment protocol for the patient.

However, there are times when it is desirable to obtain a 2D representation of the 3D pain/stimulation map. For instance, the 3D pain/stimulation maps are typically data-intensive (i.e., they may be large files), which make their sharing difficult. As a result, may take an excessively long period of time to upload a 3D pain map from a clinician programmer to a remote database, and/or to download that pain map from that database to a clinician programmer. In comparison, a 2D pain/stimulation map is typically much less data-intensive (e.g., with a percent of the data for a 3D pain/stimulation map) and as such can be easily shared. As another example, 3D pain/stimulation maps may not be easily printed. Thus, it may be desirable to print a 2D representation of the 3D pain/stimulation map. The following discussions describe how to obtain a 2D representation of a 3D pain/stimulation map according to the various aspects of the present disclosure.

At least two types of 2D pain/stimulation maps may be obtained from a 3D pain/stimulation map. One type of the 2D pain/stimulation map is derived as a "snapshot" (also referred to as a projection) of the 3D pain/stimulation map. The "snapshot" type 2D pain/stimulation map may be obtained by rotating the 3D pain/stimulation map to a suitable perspective or viewing angle, and then projecting the 3D pain/stimulation map to a flat surface. Thus, the "snapshot" 2D pain/stimulation map is a projection of the 3D human body model with the pain/stimulation map drawn on it. Alternatively stated, the "snapshot" 2D pain/stimulation map captures an instantaneous picture of the 3D pain/stimulation map, as seen by a person viewing the 3D pain/stimulation map at that time.

Another type of the 2D pain/stimulation map is derived as a "wrapping texture" or a "wrap cloth" of the 3D pain/stimulation map. This is done by showing an entire surface area of the 3D human body model (or a selected portion thereof) by flattening or completely stretching it out. The 3D pain/stimulation map on the body model is therefore flattened or stretched out too. Another way of looking at the generation of the "wrapping texture" type 2D pain/stimulation map is that, a two-dimensional flat digital "cloth" is wrapped around the 3D human body model. As such, the cloth takes after the shape and contours of the 3D human body model. The patient then paints the pain/stimulation map on this piece of digital "cloth." The resulting pain/stimulation map therefore exhibits 3D characteristics as long as the cloth itself is wrapped around the 3D human body model. To obtain the 2D pain/stimulation map, the digital cloth is removed from the 3D body model and flattened or stretched out. At this point, the digital cloth returns to a 2D form. Consequently, the painted pain/stimulation regions on the digital cloth now also flat and exhibits 2D characteristics. It is understood that the digital cloth may be a single piece of cloth in some embodiments, but may also include multiple pieces of cloth in alternative embodiments.

It is understood that the 3D pain/stimulation map and the 2D pain/stimulation maps discussed above may contain reference points, which allow the 2D pain/stimulation map to match up correctly with the 3D pain/stimulation map. For example, in order to reconstruct a 3D pain/stimulation map from one or more 2D pain/stimulation maps, their respective reference points should match up.

Regardless of which type of 2D pain/stimulation map is obtained, the amount of data involved for the 2D pain/stimulation map is much less than its 3D counterpart. For example, the data required for the "snapshot" type 2D pain/stimulation map only needs to be sufficient to represent a single projection of the 3D map or model, rather than needing data to represent the map or model from all different perspectives and viewing angles. As another example, for the "wrapping texture" type 2D pain/stimulation map, only the digital cloth itself may be needed for the sharing thereof. The data associated with the actual 3D human body model is not needed. In other words, in order to share the 3D pain/stimulation map, only the 2D pain/stimulation map is needed, and then the 3D pain/stimulation map may be reconstructed after the receipt of the 2D pain/stimulation map.

For instance, a patient John Doe may generate a 3D pain/stimulation map based on a predefined human body model type (e.g., a 35-year old 6'0 Caucasian male weighing 200 pounds) as discussed above. A corresponding "wrapping texture" type 2D pain/stimulation map may then be obtained by flattening the digital "cloth." The 2D pain/stimulation map may be uploaded to and saved in a remote electronic database, for example in a manner consistent with the discussions above. The actual 3D human body model need not be sent, as that 3D human body model is already available in that electronic database (or can be readily downloaded from another suitable electronic database).

Suppose now that John Doe has moved to a different part of the country. He makes a visit with a new healthcare provider. The healthcare provider may have access to the remote electronic database that includes the 3D human body model corresponding to John Doe's physiology (as well as a plurality of other predefined human body types). These body types may already be downloaded onto the healthcare provider's clinician programmer (or can be readily downloaded). Therefore, to reconstruct the 3D pain/stimulation map for John Doe, the healthcare provider merely needs to access the electronic database where the 2D digital cloth having the pain/stimulation map drawn thereon is stored. The 2D digital cloth can be quickly downloaded onto the healthcare provider's clinician programmer, since it is a 2D object and therefore is not very data-intensive. The clinician programmer can then reconstruct the 3D pain/stimulation map by "wrapping" the digital cloth on the 3D human body model corresponding to John Doe's physiology. Note that in this reconstruction process, the actual human body model need not be transmitted by John Doe's previous healthcare provider. Again, only the 2D digital cloth having the pain/stimulation map needs to be shared. The new healthcare provider just needs to locate the correct 3D human body model from the database, download the 2D digital cloth, and wrap the cloth around the 3D human body model in order to reconstruct John Doe's 3D pain/stimulation map.

It is understood that, in addition to the wrapping texture 2D pain/stimulation map, the snapshot type 2D pain/stimulation map may also be used to reconstruct the 3D pain/stimulation map. For example, a plurality of snapshot 2D pain/stimulation maps may be obtained from a 3D pain/stimulation map. Each of the snapshot 2D pain/stimulation maps may represent a different perspective or a different angle. Later on, these snapshot 2D pain/stimulation maps may be collectively used to piece together the original 3D pain/stimulation map.

FIGS. 19-23 are example screenshots of a user interface 350 for viewing 3D and 2D pain/stimulations maps according to the various aspects of the present disclosure. In some embodiments, the user interface 350 may be displayed on a screen of a programmer, for example a capacitive or resistive touch-sensitive display.

Figure 19B:
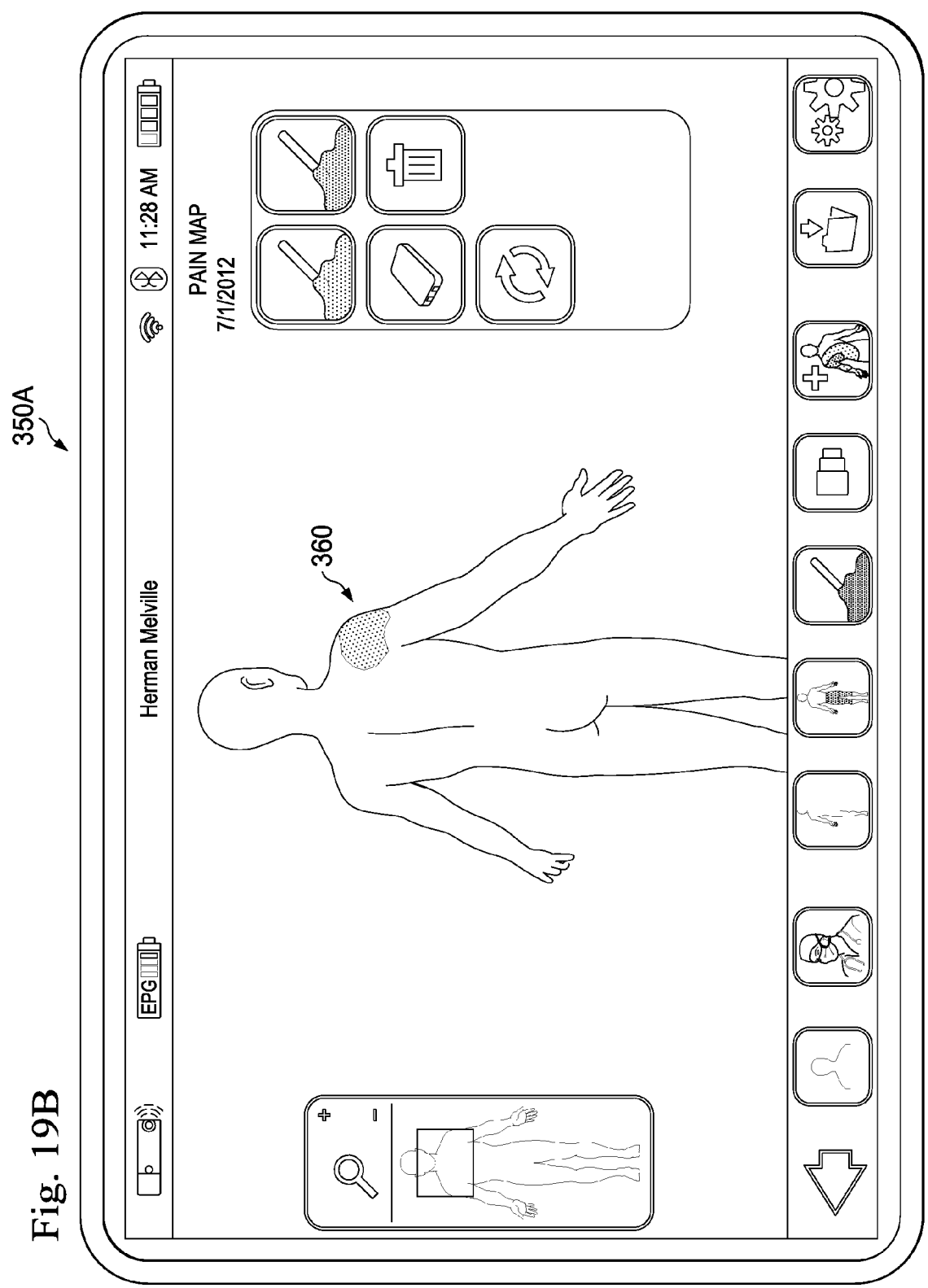

Referring to FIGS. 19A-19B, the user interface 350A illustrates an example 3D pain map 360 from two different perspective angles. In the illustrated embodiment, the pain map 360 is located in or near a right shoulder of the 3D human body model. After the 3D pain map 360 is completed, 2D representations of the 3D pain map may be generated, for example by clicking a virtual button (not illustrated herein) in the interface 350.

Figure 20:
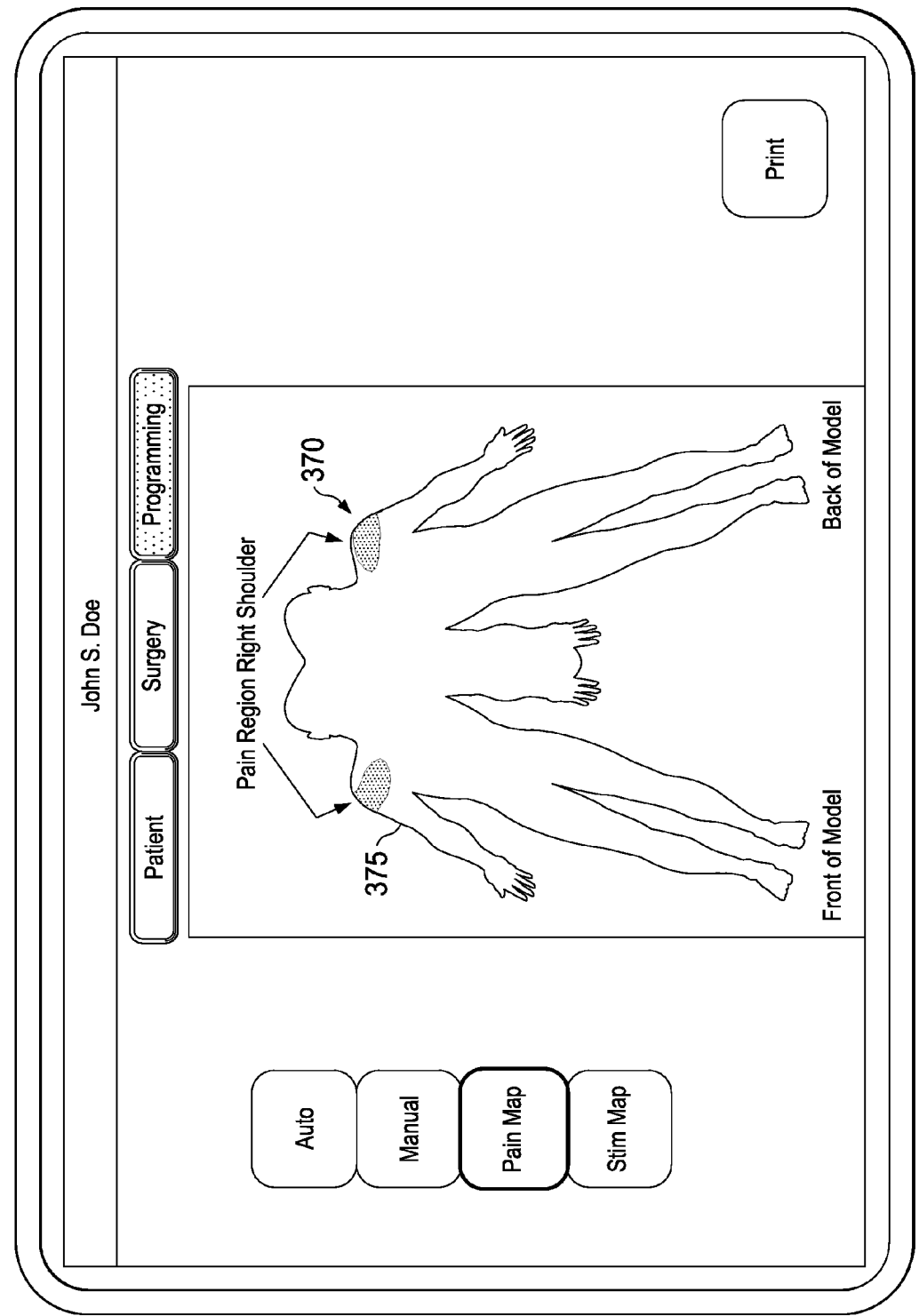

An example of the 2D pain map corresponding to the 3D pain map 360 is shown in FIG. 20. The user interface 350B shows a 2D pain map 370 that is a "flattened" version of the 3D pain map 360. In other words, the 2D pain map 370 is a wrapping texture type 2D pain map. A digital "cloth" 375 is used to wrap around the 3D human body model. The pain region is drawn on the digital cloth 375. Therefore, the 2D pain map 370 is obtained when the digital cloth 375 is flattened to its 2D form. In some embodiments, the digital cloth is flattened into the 2D form by splitting the 3D human body model along the vertices (defining the shape of the 3D model) on the side of the model.

The 2D pain map 370 of FIG. 20 contains substantially less data than the 3D pain map 360 of FIGS. 19A-19B. In some embodiments, the 2D pain map 370 has less than 10% of the data associated with the 3D pain map 360. Therefore, the 2D pain map 370 can be easily shared over a network or printed. To reconstruct the 3D pain map 360, an electronic programmer merely needs to download the 2D pain map 370 and apply it over the same 3D human model on which it was originally created. As discussed above, the particular 3D human body model may be selected from a list of predefined human body models from a database. These predefined human body models each have a set of unique physical characteristics, such as height, weight, age, gender, body build, or ethnicity.

Figure 21:
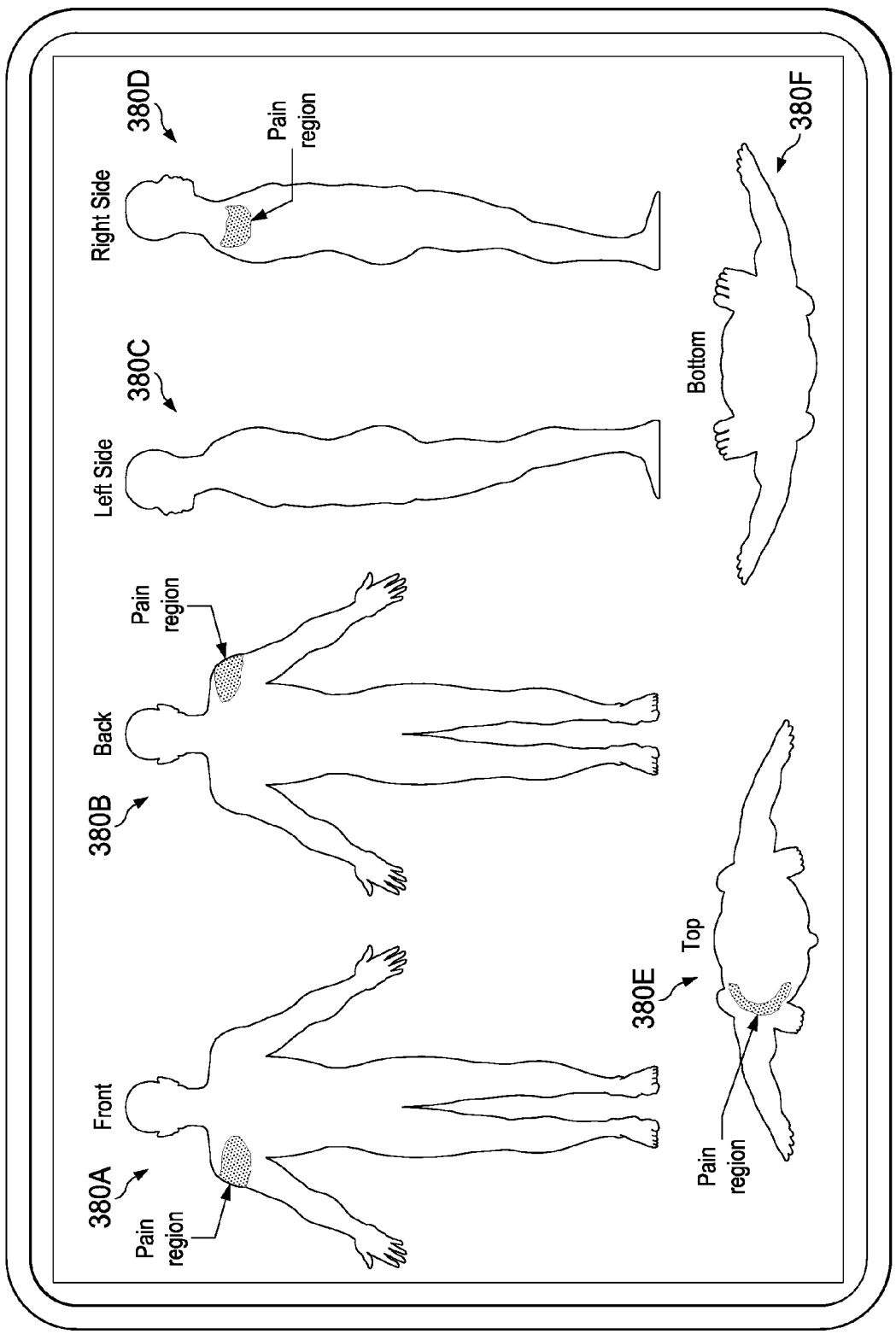

Another example of the 2D pain map corresponding to the 3D pain map 360 is shown in FIG. 21. The user interface 350C shows various 2D "snapshot" type pain maps 380A-380F of the 3D pain map 360 taken at different angles. The snapshot 2D pain map 380A is derived by projecting the front of the 3D pain map 360 to a flat surface, the snapshot 2D pain map 380B is derived by projecting the back of the 3D pain map 360 to a flat surface, the snapshot 2D pain map 380C is derived by projecting the left side of the 3D pain map 360 to a flat surface, the snapshot 2D pain map 380D is derived by projecting the right side of the 3D pain map 360 to a flat surface, the snapshot 2D pain map 380E is derived by projecting the top of the 3D pain map 360 to a flat surface, and the snapshot 2D pain map 380F is derived by projecting the feet of the 3D pain map 360 to a flat surface. The pain region (near the right shoulder) that appears in FIGS. 19A-19B and 20 are also visible in FIG. 21 on the 2D snapshots 380A-380B and 380D-380E. Again, these 2D pain maps 380A-380F contain substantially less data than the 3D pain map 360. Therefore, the printing and sharing of these 2D pain maps 380A-380D are much easier than the printing and sharing of the 3D pain maps. Of course, the discussions above also apply to 3D and 2D stimulation maps.

The present disclosure also allows for custom-zoomed printed regions. To illustrate, an example 3D pain map 390 is shown by the user interface 350D in FIG. 22. The pain region is on the left food and a lower left leg portion in the illustrated embodiment. Thus, for a more detailed view of the pain region, the user interface 350D zooms in to a portion of the lower left leg portion of the human body model. If additional detail is needed, the user interface 350D allows for further zooming. In addition, the user interface 350D allows for rotation repositioning of the part of the human body model showing the 3D pain map 390 as well.

Figure 22:
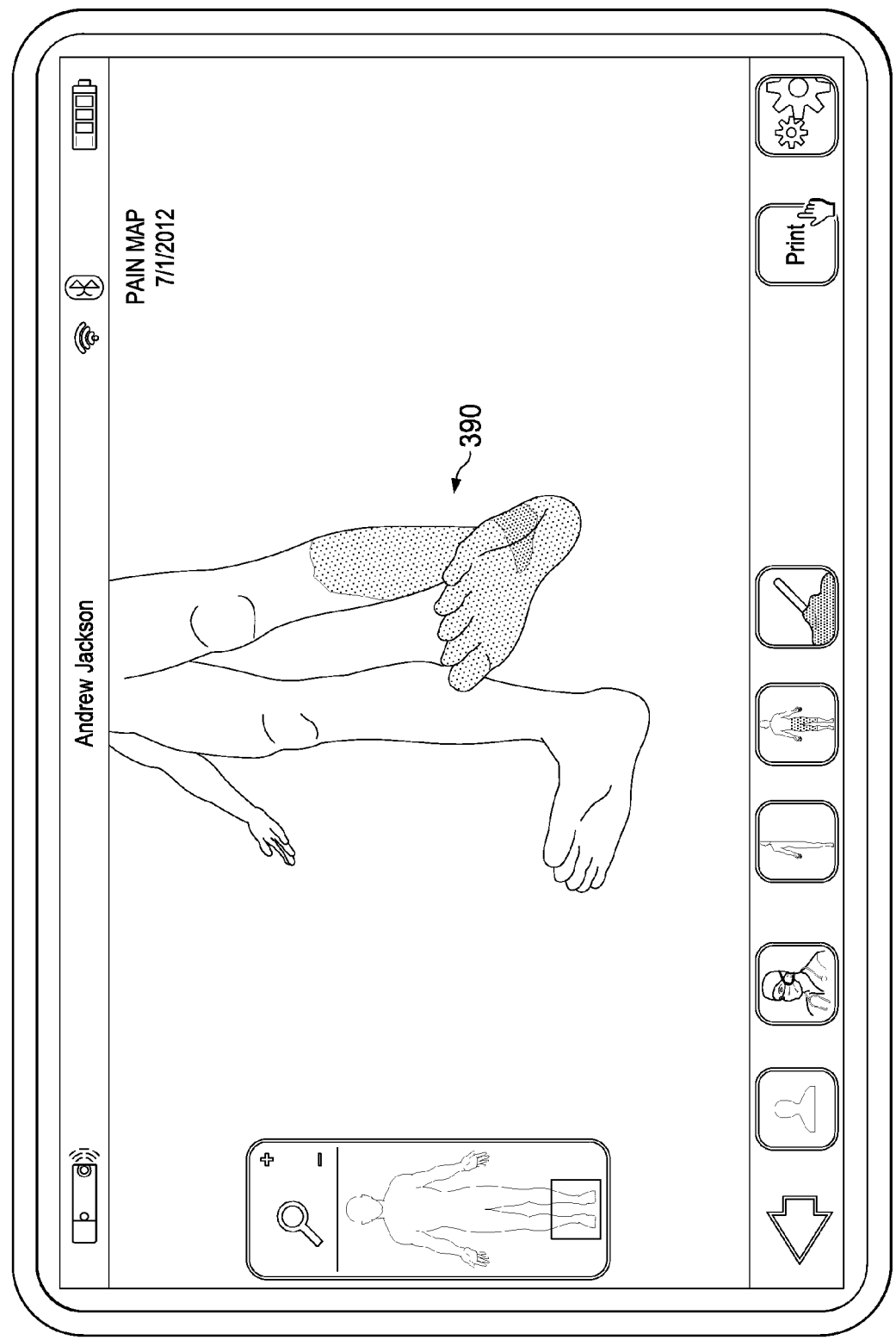
Figure 23:
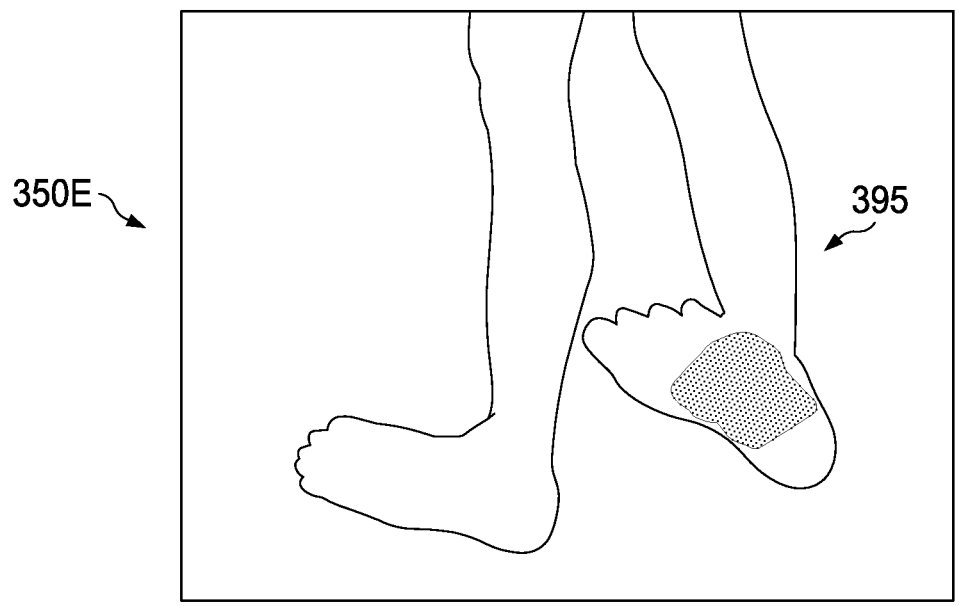

Referring now to FIG. 23, the user interface 350E shows a 2D pain map 395 that is derived from the 3D pain map 390 of FIG. 22. As was the case with the 3D pain map 390, the 2D pain map 395 also includes a "zoomed in" view near the left foot and lower leg of the human body model. As discussed above, this custom zoomed 2D pain map 395 is easier to print and share, which is at least in part due to its much smaller data size compared to its 3D counterpart.

Figure 24:
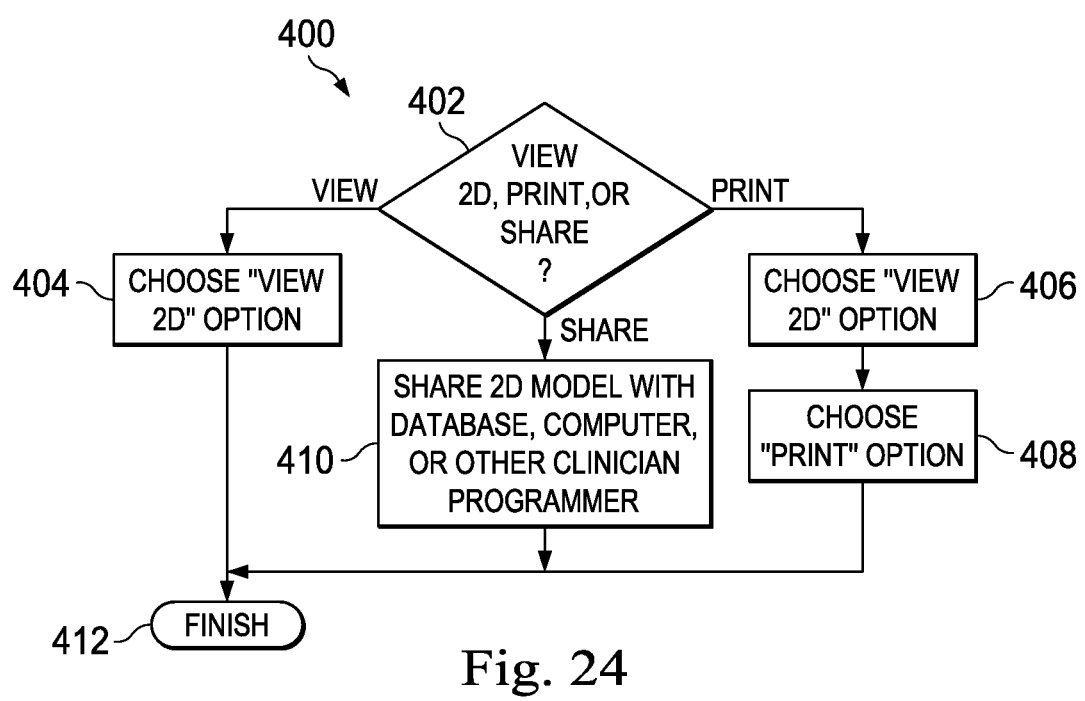
Figure 25:
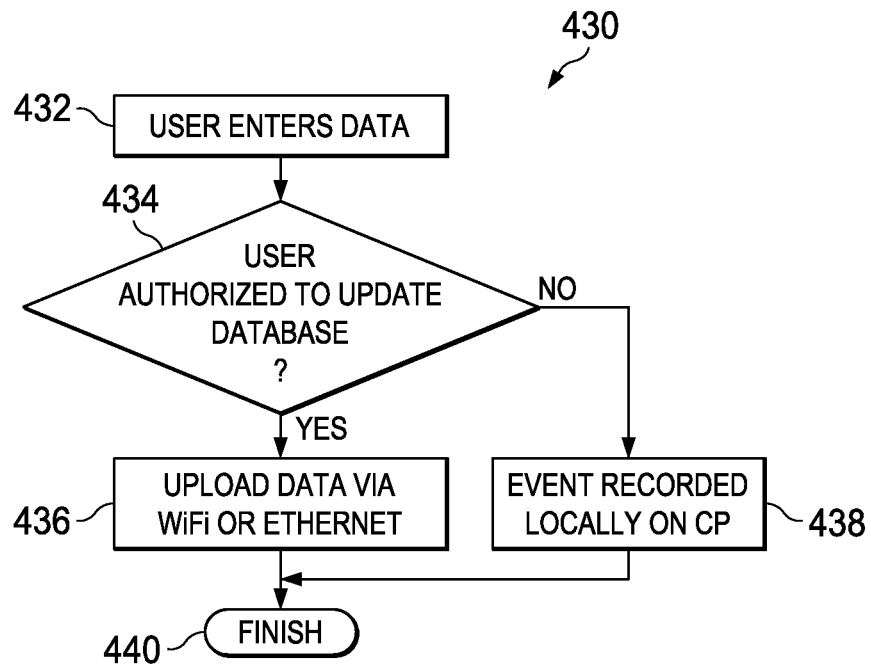
Figure 26:
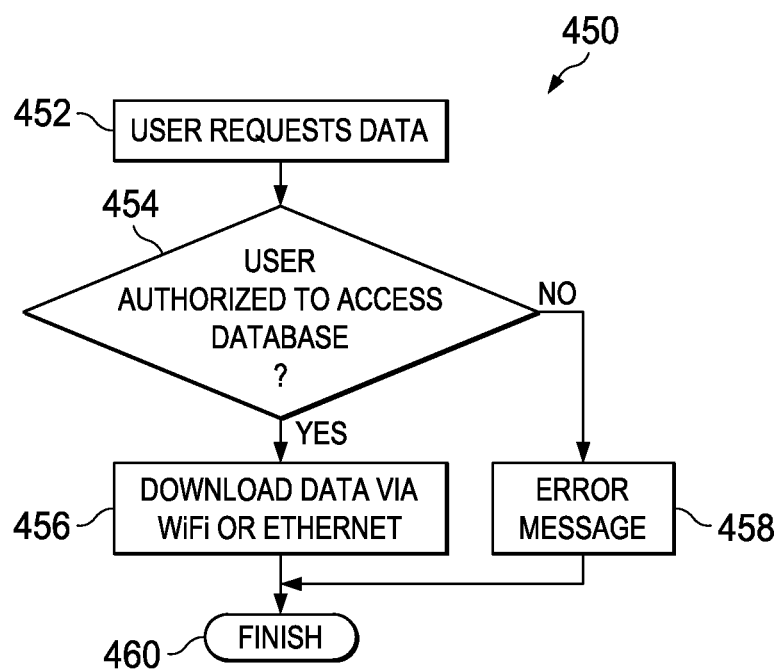

FIGS. 24-26 are flowcharts of various methods of generating, manipulating, and sharing the 3D pain and stimulation maps according to the various aspects of the present disclosure. It is understood that the flowcharts shown in FIG. 24-26 have been simplified for a better understanding of the inventive concepts of the present disclosure. Accordingly, it should be noted that additional processes may be provided before, during, and after the methods of FIGS. 24-26, and that some other processes may only be briefly described herein.

Referring to FIG. 24, a method 400 is an example flowchart for viewing, printing, and sharing 2D representations and 3D models according to the various aspects of the present disclosure. It is assumed that the 3D pain/stimulation map has already been generated on an electronic programmer (e.g., a clinician programmer) before the method 400 is performed. The method 400 includes a decision step 402 to determine whether a user would like to view, or print, or share a 2D counterpart of the 3D pain/stimulation map. If the answer from the decision step 402 is that the user wishes to view a 2D pain/stimulation map, the method 400 proceeds to step 404, in which a 2D pain/stimulation map is derived from the 3D pain/stimulation map, for example by the user clicking on a "view 2D option" button on the electronic programmer. If the answer from the decision step 402 is that the user wishes to print a 2D pain/stimulation map, the method proceeds to step 406, which may be similar to the step 404. In other words, a 2D pain/stimulation map is derived from the 3D pain/stimulation map. Thereafter, the method 400 proceeds to step 408 to print the 2D pain/stimulation map. If the answer from the decision step 402 is that the user wishes to share a 2D pain/stimulation map, the method 400 proceeds to step 410, in which a 2D pain/stimulation map is generated and then subsequently sent to a remote database, a local computer storage device, or another electronic programmer. The sharing may take place over a suitable telecommunications network, for example. The method 400 concludes at step 412.

Referring now to FIG. 25, a method 430 describes an example process flow for uploading a 2D representation of a 3D pain/stimulation map to a database. The method 430 includes a step 432, in which a user attempts to enter data into the database. The data may include the 2D pain/stimulation map, for example. The method 430 continues with a decision step 434 to determine whether the user is authorized to update the database. If the answer is yes, then the data is allowed to be uploaded to the database, for example via a Wi-Fi or Ethernet network. On the other hand, if the user does not have the right to access or update the database, the method 430 proceeds to step 438, in which the event (i.e., the attempt by the user to upload the data to the database) is recorded locally on the electronic programmer. In this case, the 2D pain/stimulation map may be saved locally on the electronic programmer. The method 430 concludes with step 440.

Referring now to FIG. 26, a method 450 describes an example process flow for downloading a 2D representation of a 3D pain/stimulation map from a database. The method 450 includes a step 452, in which a user attempts to request data to be downloaded from a database, for example the database discussed above with reference to FIG. 25 in which the data was uploaded. The data may include the 2D pain/stimulation map, for example.

The method 450 continues with a decision step 454 to determine whether the user is authorized to access the database. If the answer is yes, then the data is allowed to be downloaded to a local device such as a clinician programmer. The downloading may take place via a Wi-Fi or Ethernet network, or via another suitable telecommunications network. On the other hand, if the user does not have the right to access the database, the method 450 proceeds to step 458, in which an error message may be displayed. The method 450 concludes with step 460.

Figure 27:
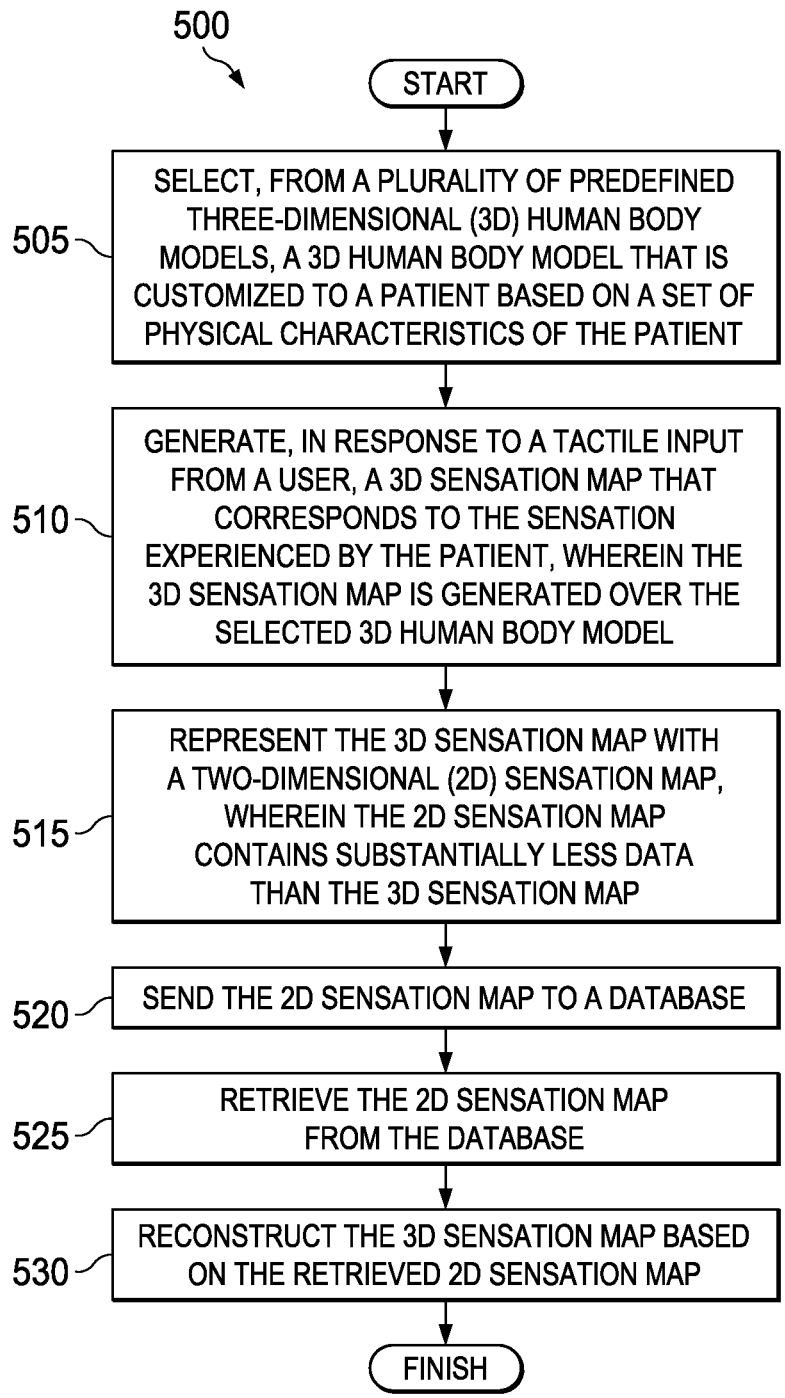

FIG. 27 is a flowchart illustrating an example process flow for graphically representing a sensation such as pain or stimulation experienced by a patient. The method 500 includes a step 505, in which a 3D human body is selected from a plurality of predefined three-dimensional (3D) human body models. The selected 3D human body model is customized to the patient based on a set of physical characteristics of the patient. In some other embodiments, the plurality of predefined 3D human body models is stored in the database. In some other embodiments, the plurality of predefined 3D human body models each have a unique set of physical characteristics including one or more of the following: height, weight, age, gender, and ethnicity. In some other embodiments, the selected 3D human body model has a closest physical characteristics match with the patient.

The method 500 includes a step 510, in which a 3D sensation map that corresponds to the sensation experienced by the patient is generated in response to a tactile input from a user. The 3D sensation map is generated over the selected 3D human body model. In some embodiments, the step 510 includes wrapping a digital cloth around the selected 3D human body model, wherein the digital cloth contains one or more sensation regions drawn by the user. The 3D sensation map includes at least one of: a 3D pain map that includes a 3D visualization of a pain experienced by the patient in a first body region of the patient; and a 3D stimulation map that includes a 3D visualization of a stimulation experienced by the patient in a second body region of the patient. In some embodiments, the user is the patient. In other embodiments, the user may be a healthcare professional.

The method 500 includes a step 515, in which the 3D sensation map is represented with a two-dimensional (2D) sensation map. The 2D sensation map contains substantially less data than the 3D sensation map. For example, in some embodiments, the 2D sensation map contains less than 20% of the data associated with the 3D sensation map. In some embodiments, the 2D sensation map may contain about 1%-10% of the data associated with the 3D sensation map. In some embodiments, the step 515 includes taking the digital cloth off of the selected 3D human body model and flattening the digital cloth to a 2D form. In some other embodiments, the step 515 includes projecting the 3D sensation map onto a flat surface.

The method 500 includes a step 520, in which the 2D sensation map is sent to a database.

The method 500 includes a step 525, in which the 2D sensation map is retrieved from the database.

The method 500 includes a step 530, in which the 3D sensation map is reconstructed based on the retried 2D sensation map. In some embodiments, the step 530 is performed using the selected 3D human body model.

In some embodiments, the steps 505-520 are performed by a first portable electronic device, and the steps 525-530 are performed by a second portable electronic device. The first and second portable electronic devices may each include one of: a clinician programmer, a patient programmer, and a computer tablet, and wherein the first and second electronic devices are configured to communicate with external devices according to a wired or wireless communications protocol.

Figure 28:
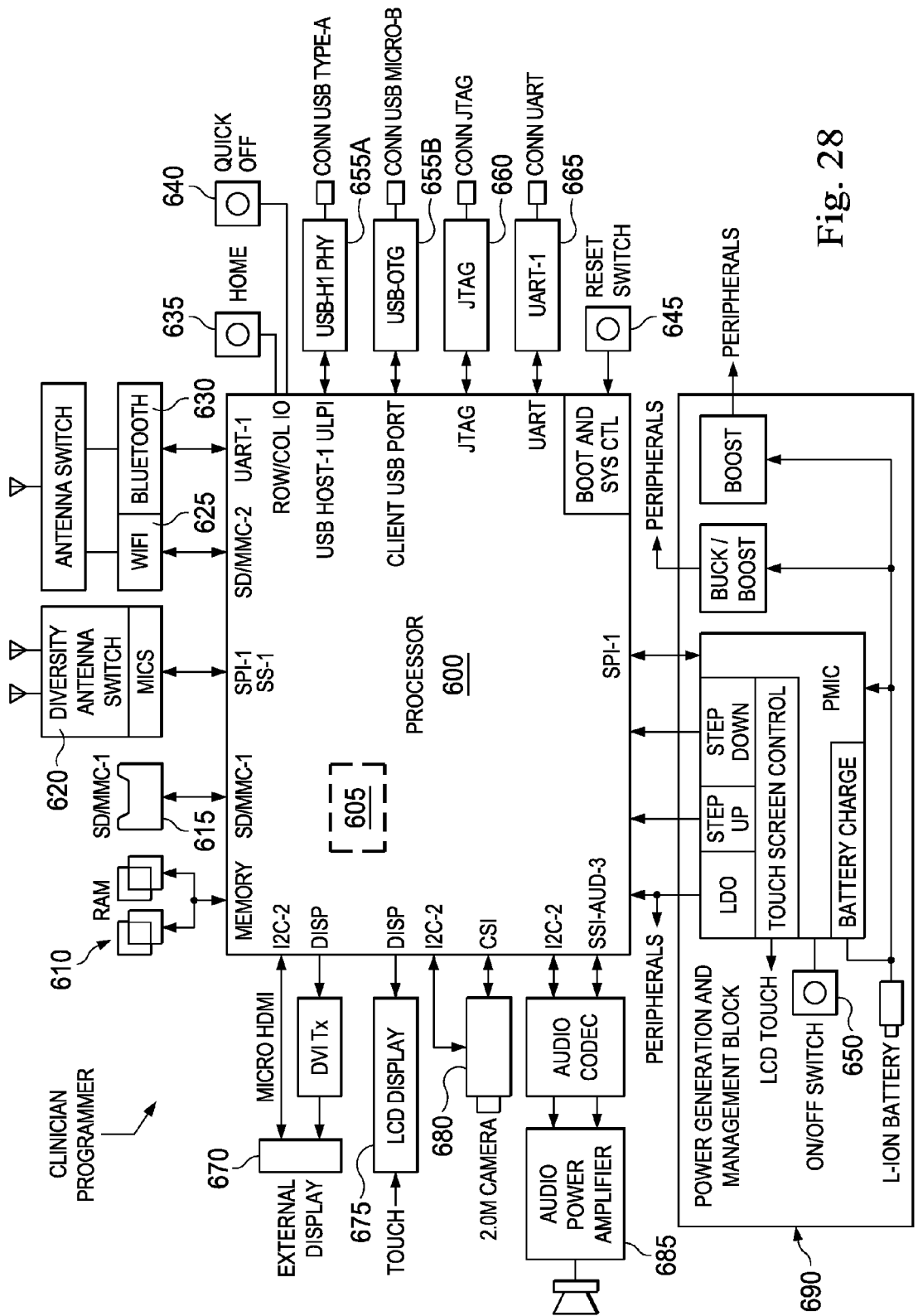
FIG. 28 is a simplified block diagram of an electronic programmer according to various aspects of the present disclosure.

FIG. 28 shows a block diagram of one embodiment of the electronic programmer (CP) discussed herein. For example, the electronic programmer may be a clinician programmer (CP) configured to generate display and display the 3D and 2D pain/stimulation maps discussed above. It is understood, however, that alternative embodiments of the electronic programmer may be used to perform these representations as well.

The CP includes a printed circuit board ("PCB") that is populated with a plurality of electrical and electronic components that provide power, operational control, and protection to the CP. With reference to FIG. 28, the CP includes a processor 600. The processor 600 controls the CP. In one construction, the processor 600 is an applications processor model i.MX515 available from Free scale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX510EC, Rev. 4" data sheet dated August 2010 and published by Free scale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 28 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 28.

The CP includes multiple bi-directional radio communication capabilities. Specific wireless portions included with the CP are a Medical Implant Communication Service (MICS) bi-directional radio communication portion 620, a Wi-Fi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The Wi-Fi portion 625 and Bluetooth portion 630 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity, including a Type A port 655A and a Micro-B port 655B; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 28.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 28) may also be included for data transfer.

It is understood that a patient programmer may be implemented in a similar manner as the clinician programmer shown in FIG. 28.

Figure 29:
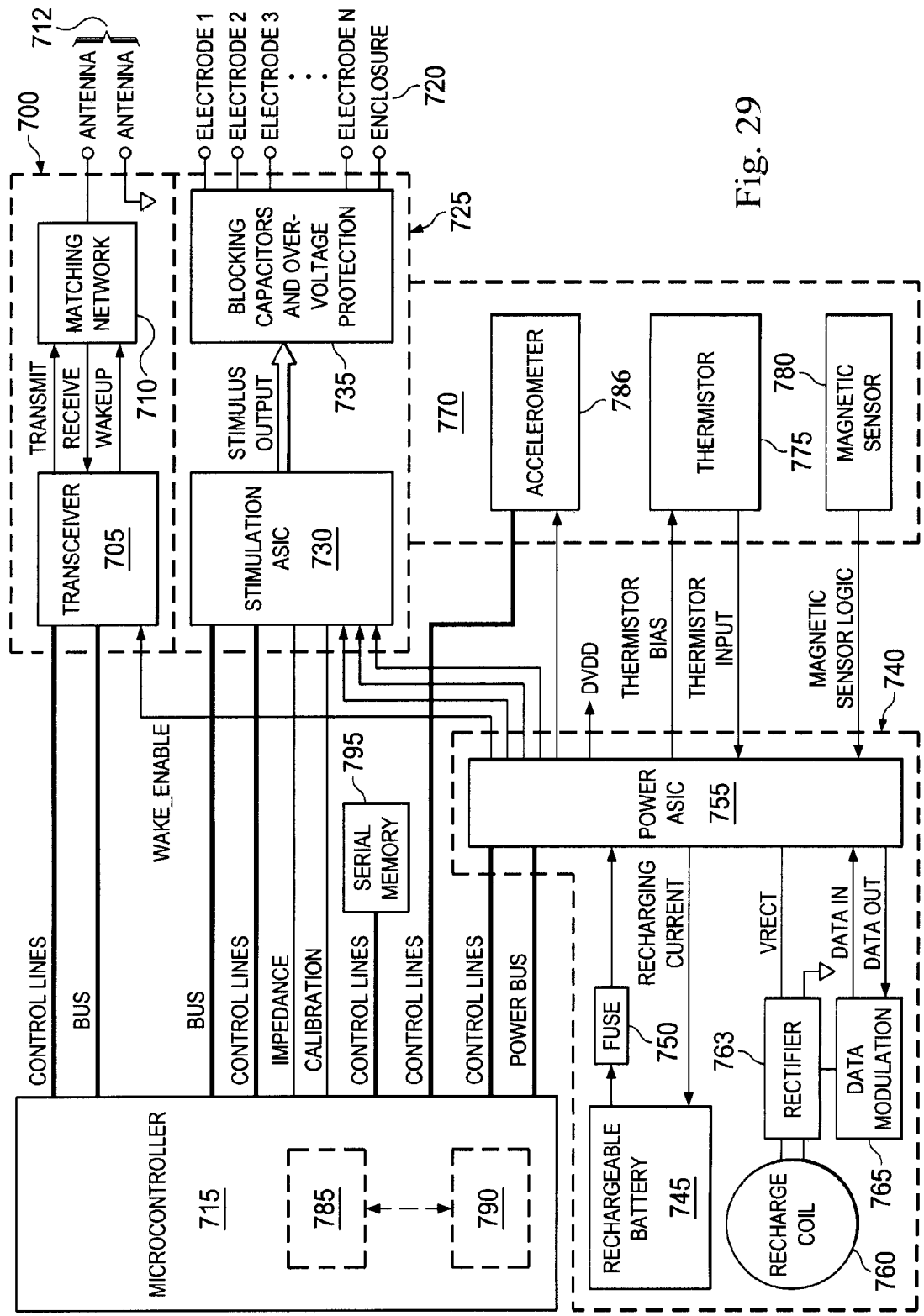
FIG. 29 is a simplified block diagram of an implantable medical device according to various aspects of the present disclosure.

FIG. 29 shows a block diagram of one embodiment of an implantable medical device. In the embodiment shown in FIG. 29, the implantable medical device includes an implantable pulse generator (IPG). The IPG includes a printed circuit board ("PCB") that is populated with a plurality of electrical and electronic components that provide power, operational control, and protection to the IPG. With reference to FIG. 29, the IPG includes a communication portion 700 having a transceiver 705, a matching network 710, and antenna 712. The communication portion 700 receives power from a power ASIC (discussed below), and communicates information to/from the microcontroller 715 and a device (e.g., the CP) external to the IPG. For example, the IPG can provide bi-direction radio communication capabilities, including Medical Implant Communication Service (MICS) bi-direction radio communication following the MICS specification.

The IPG provides stimuli to electrodes of an implanted medical electrical lead (not illustrated herein). As shown in FIG. 29, N electrodes are connected to the IPG. In addition, the enclosure or housing 720 of the IPG can act as an electrode. The stimuli are provided by a stimulation portion 725 in response to commands from the microcontroller 715. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, FLASH, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a portion 770 that includes an accelerometer 786, and thermistor 775, and magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 29 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP430 mixed signal processor can be found in, for example, the "MSP430G2x 32, MSP430G2x02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a signal from the CP.

Figure 30:
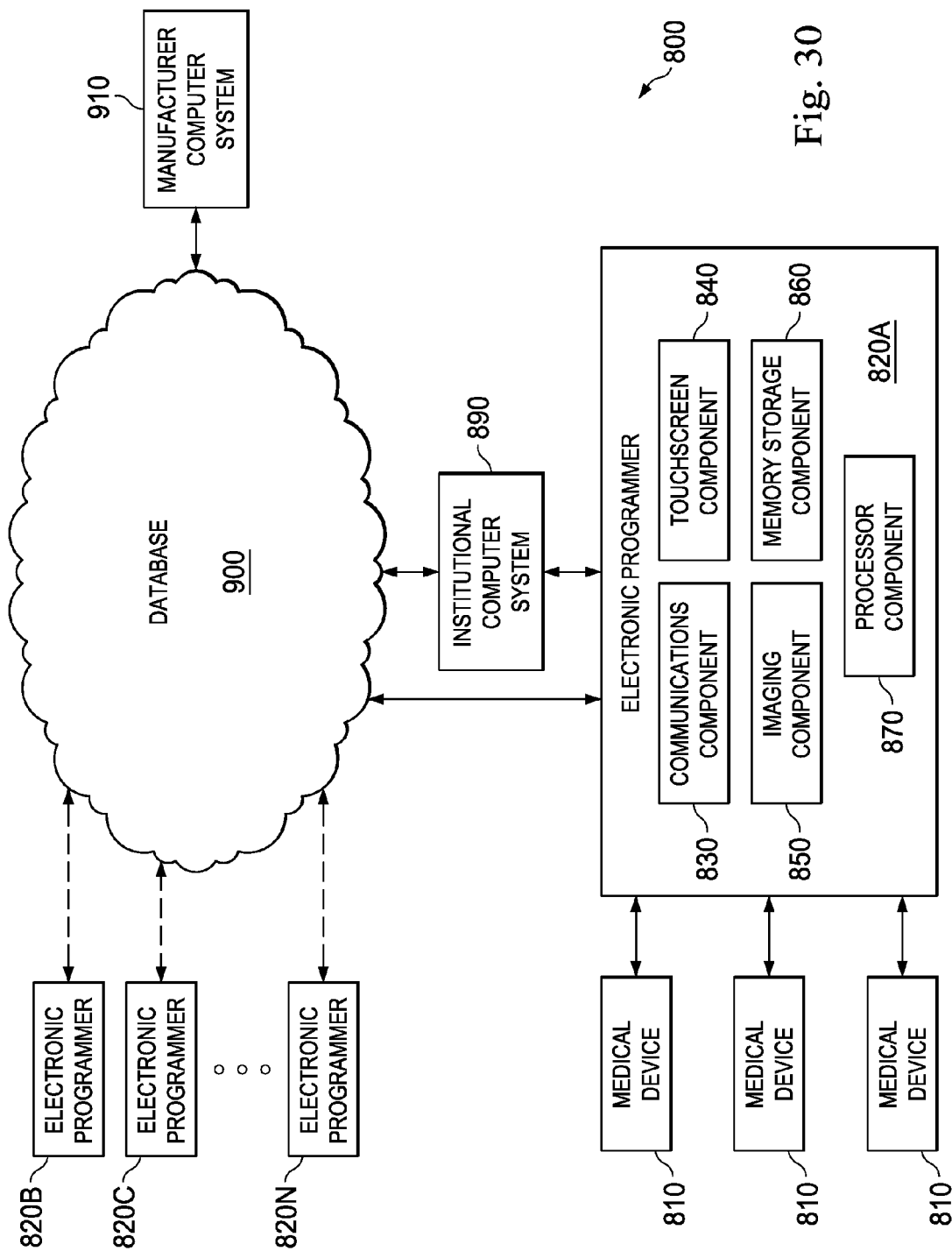
FIG. 30 is a simplified block diagram of a medical system/infrastructure according to various aspects of the present disclosure.

Referring now to FIG. 30, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above with reference to FIG. 1. For example, the medical devices 810 may be a pulse generator (e.g., the IPG discussed above with reference to FIG. 29), an implantable lead, a charger, or portions thereof. It is understood that each of the medical devices 810 may be a different type of medical device. In other words, the medical devices 810 need not be the same type of medical device.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIG. 28. In other embodiments, the electronic programmer 820A may be a patient programmer or another similar programmer. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 30 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, the pain/stimulation maps may be uploaded from the electronic programmer 820A to the database 900. The pain/stimulation maps saved in the database 900 may thereafter be downloaded by any of the other electronic programmers 820B, 820C-820N communicatively coupled to it, assuming the user of these programmers has the right login permissions. For example, after the 2D pain/stimulation map is generated by the electronic programmer 820A and uploaded to the database 900. That 2D pain/stimulation map can then be downloaded by the electronic programmer 820B, which can use the downloaded 2D pain/stimulation map to reconstruct or recreate a 3D pain/stimulation map. In this manner, a less data-intensive 2D pain/stimulation map may be derived from a data-heavy 3D pain/stimulation map, sent to a different programmer through the database, and then be used to reconstruct the 3D pain/stimulation map.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

Figure 31B:
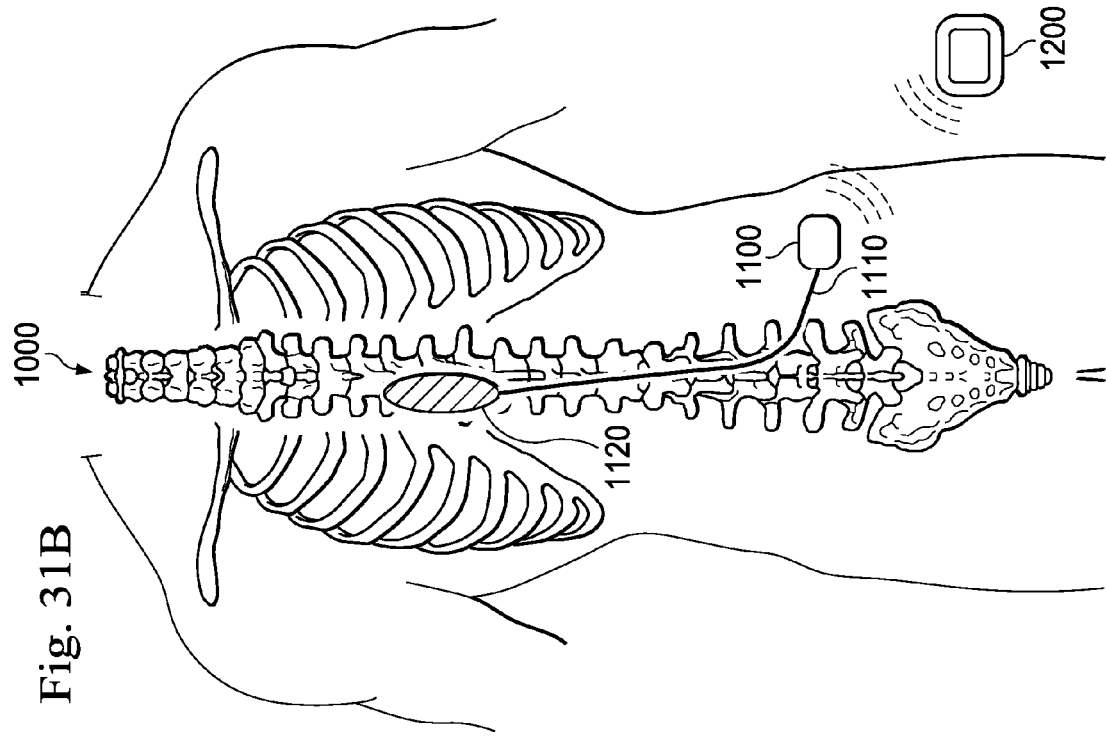
FIGS. 31A and 31B are side and posterior views of a human spine, respectively.
Figure 31A:
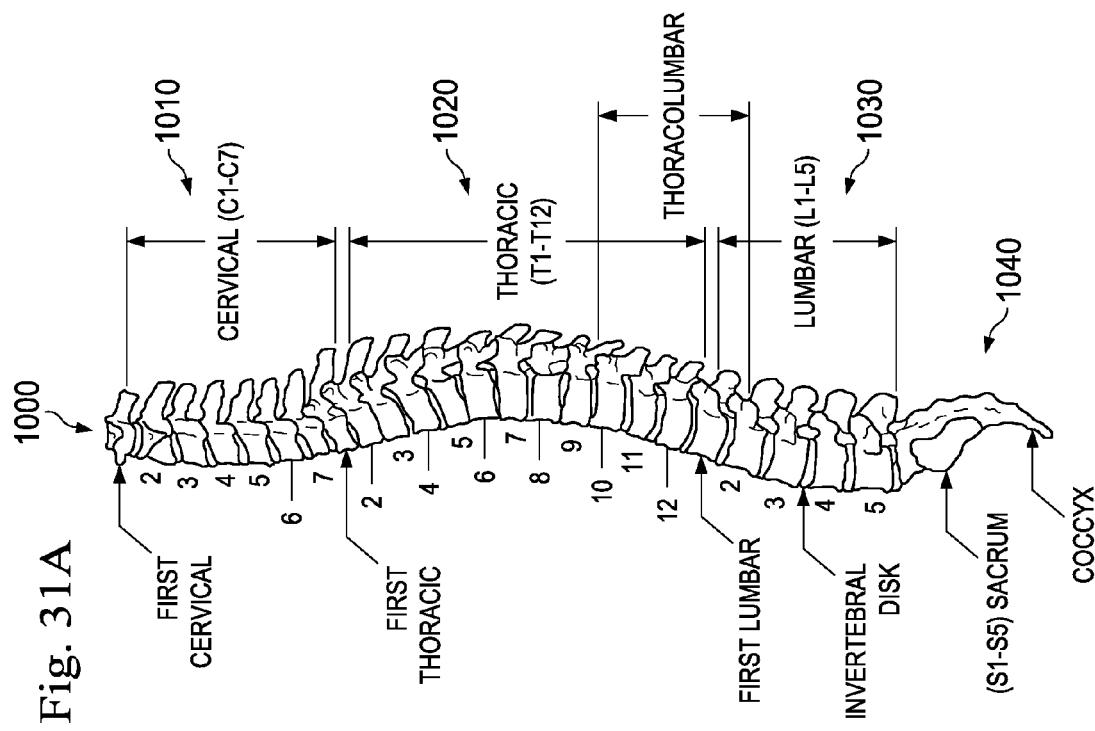

FIG. 31A is a side view of a spine 1000, and FIG. 31B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 31B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 28.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An electronic device for visualizing a sensation experienced by a patient, the electronic device comprising:
   a user interface configured to receive a tactile input from a user and display a visual output;
   a memory storage component configured to store programming code; and
   a computer processor configured to execute the programming code to perform the following tasks:
      selecting, in response to a user input and from an electronic database offering a plurality of predefined human body models that each have a unique set of physical characteristics, a human body model that most closely matches physical characteristics of the patient;
      offering, via the user interface, the user one or more options on adjusting one or more of the physical characteristics of the selected human body model;
      detecting, via the user interface, an adjustment of a physical characteristic of the selected human body model;
      adjusting, in response to the detected adjustment, the physical characteristic of the selected human body model;
      generating, in response to the tactile input from the user, a three-dimensional (3D) sensation map over the selected human body model having the adjusted physical characteristic, the 3D sensation map including a pain map representing a pain sensation experienced by the patient and a stimulation map representing a stimulation sensation experienced by the patient;
      displaying an area of the pain map that is not covered by the stimulation map without displaying an overlapped area between the pain map and the stimulation map;
      deriving a two-dimensional (2D) sensation map based on the 3D sensation map, wherein the 2D sensation map contains substantially less data than the 3D sensation map; and
      sending the 2D sensation map over a network to facilitate a reconstruction of the 3D sensation map using the 2D sensation map and the selected human body model having the adjusted physical characteristic.

2. The electronic device of claim 1, wherein the deriving the 2D sensation map comprises deriving a snapshot type 2D sensation map that includes a projection of the 3D sensation map on a flat surface.

3. The electronic device of claim 1, wherein the deriving the 2D sensation map comprises deriving a wrapping texture type 2D sensation map, the wrapping texture type 2D sensation map including a 2D digital cloth configured to be wrapped around a 3D human body model, and wherein the 2D digital cloth contains one or more sensation regions drawn by the patient.

4. The electronic device of claim 3, wherein the sending the 2D sensation map comprises saving the 2D digital cloth to a remote electronic database, and wherein the 2D digital cloth is configured for downloading by one of the electronic devices on which the 3D sensation map is to be reconstructed.

5. The electronic device of claim 1, wherein the tasks further comprise:
   receiving a further 2D sensation map; and
   reconstructing a further 3D sensation map using the further 2D sensation map.

6. The electronic device of claim 1,
   wherein the pain map is a 3D pain map that includes a 3D visualization of a pain experienced by the patient in a first body region of the patient; and
   wherein the stimulation map is a 3D stimulation map that includes a 3D visualization of a stimulation experienced by the patient in a second body region of the patient.

7. The electronic device of claim 1, wherein the electronic device is one of: a clinician programmer, a patient programmer, and a computer tablet, and wherein the electronic device is portable and is configured to communicate with external devices according to a wired or wireless communications protocol.

8. A medical system, comprising:
   an electronic database storing a plurality of predefined human body models that each have a unique set of physical characteristics;
   a first portable electronic device that includes:
      a user interface configured to receive a tactile input from a user and display a visual output;
      a first electronic processing component configured to:
         select, from the electronic database in response to a user input, one of the predefined human body models that most closely matches physical characteristics of a patient;
         offer, via the user interface, the user one or more options on adjusting one or more of the physical characteristics of the selected human body model;
         detect, via the user interface, an adjustment of a physical characteristic of the selected human body model;
         adjust, in response to the detected adjustment, the physical characteristic of the selected human body model;

generate a three-dimensional (3D) sensation map over the selected human body model having the adjusted characteristic, the sensation map including a pain map representing a pain sensation experienced by the patient and a stimulation map representing a stimulation sensation experienced by the patient;

displaying an area of the pain map that is not covered by the stimulation map without displaying an overlapped area between the pain map and the stimulation map;

produce a two-dimensional (2D) sensation map that is a 2D representation of the 3D sensation map for the patient, the 2D sensation map containing less data than the 3D sensation map; and a first communications interface configured to send the 2D sensation map to the electronic database; and a second portable electronic device that includes:

a second communications interface configured to receive the 2D sensation map and the selected human body model from the electronic database;

a second electronic processing component configured to reproduce the 3D sensation map based on the 2D sensation map and the selected human body model; and a second user interface configured to display at least one of the 2D sensation map received from the electronic database or the reproduced 3D sensation map.

9. The medical system of claim 8, wherein the 2D sensation map includes a snapshot type 2D sensation map that is a projection of the 3D sensation map on a flat surface.

10. The medical system of claim 8, wherein the 2D sensation map include a wrapping texture type 2D sensation map, the wrapping texture type 2D sensation map including a 2D digital cloth configured to be wrapped around a 3D human body model, and wherein the 2D digital cloth contains one or more sensation regions drawn by the patient.

11. The medical system of claim 8,
wherein the pain map is a 3D pain map that includes a 3D visualization of a pain experienced by the patient in a first body region of the patient; and
wherein the stimulation map is a 3D stimulation map that includes a 3D visualization of a stimulation experienced by the patient in a second body region of the patient.

12. The medical system of claim 8, wherein the first and second portable electronic devices each include one of: a clinician programmer, a patient programmer, and a computer tablet.

13. A method of representing a sensation experienced by a patient, comprising:
selecting, in response to a user input and from an electronic database offering a plurality of predefined three-dimensional (3D) human body models that each have a unique set of physical characteristics, a human body model that most closely matches physical characteristics of the patient;
offering, via a user interface, a user one or more options on adjusting one or more of the physical characteristics of the selected human body model;
detecting, via the user interface, an adjustment of a physical characteristic of the selected human body model;
adjusting, in response to the detected adjustment, the physical characteristics of the selected human body model;

generating, in response to a tactile input from the user, a 3D sensation map that includes a pain map corresponding to a pain sensation experienced by the patient and a stimulation map corresponding to a stimulation sensation experienced by the patient, and wherein the 3D sensation map is generated over the selected 3D human body model having the adjusted physical characteristic;

displaying an area of the pain map that is not covered by the stimulation map without displaying an overlapped area between the pain map and the stimulation map;

representing the 3D sensation map with a two-dimensional (2D) sensation map, wherein the 2D sensation map contains substantially less data than the 3D sensation map; and facilitating a reconstruction of the 3D sensation map based on the 2D sensation map and the selected human body model having the adjusted physical characteristic.

14. The method of claim 13, wherein the facilitating comprises sending the 2D sensation map to the electronic database; and further comprising:
retrieving the 2D sensation map from the database; and
reconstructing the 3D sensation map based on the retrieved 2D sensation map.

15. The method of claim 14, wherein:
the selecting, the offering, the detecting, the adjusting, the generating, the representing, and the sending are performed by a first portable electronic device; and
the retrieving and the reconstructing are performed by a second portable electronic device.

16. The method of claim 15, wherein the first and second portable electronic devices each include one of: a clinician programmer, a patient programmer, and a computer tablet, and wherein the first and second electronic devices are configured to communicate with external devices according to a wired or wireless communications protocol.

17. The method of claim 13, wherein the generating the 3D sensation map comprises wrapping a digital cloth around the selected 3D human body model, and wherein the digital cloth contains one or more sensation regions drawn by the patient.

18. The method of claim 17, wherein the representing the 3D sensation map comprises taking the digital cloth off of the selected 3D human body model and flattening the digital cloth to a 2D form.

19. The method of claim 13, wherein the representing the 3D sensation map comprises projecting the 3D sensation map onto a flat surface.

20. The method of claim 13,
wherein the pain map is a 3D pain map that includes a 3D visualization of a pain experienced by the patient in a first body region of the patient; and
wherein the stimulation map is a 3D stimulation map that includes a 3D visualization of a stimulation experienced by the patient in a second body region of the patient.

21. A portable electronic apparatus, comprising:
means for selecting, in response to a user input and from an electronic database offering a plurality of predefined three-dimensional (3D) human body models that each have a unique set of physical characteristics, a human body model that most closely matches physical characteristics of a patient;
means for offering a user one or more options on adjusting one or more of the physical characteristics of the selected human body model;
means for detecting an adjustment of a physical characteristic of the selected human body model by the user;

means for adjusting, in response to the detected adjustment, the physical characteristic of the selected human body model;

means for generating, in response to a tactile input from the user, a first 3D sensation map that includes a pain map that indicates a pain sensation experienced by the patient and a stimulation map that indicates a stimulation sensation experienced by the patient, wherein the first 3D sensation map is generated over the selected 3D human body model having the adjusted physical characteristic;

means for displaying an area of the pain map that is not covered by the stimulation map without displaying an overlapped area between the pain map and the stimulation map;

means for representing the first 3D sensation map with a first two-dimensional (2D) sensation map, wherein the first 2D sensation map contains substantially less data than the first 3D sensation map;

means for sending the first 2D sensation map to the electronic database and receiving a second 2D sensation map from the electronic database; and means for generating a second 3D sensation map based on the second 2D sensation map.

22. The portable electronic apparatus of claim 21, wherein the 2D sensation map includes a snapshot type 2D sensation map or a wrapping texture type 2D sensation map.

23. The portable electronic apparatus of claim 21, further comprising means for conducting electronic communications with external devices according to a wired or wireless communications protocol.

24. The portable electronic apparatus of claim 21,
wherein the pain map is a 3D pain map that includes a 3D visualization of a pain experienced by the patient in a first body region of the patient; and
wherein the stimulation map is a 3D stimulation map that includes a 3D visualization of a stimulation experienced by the patient in a second body region of the patient.

25. The portable electronic apparatus of claim 21, wherein the second 2D sensation map is uploaded to the database by a further portable electronic apparatus.

26. The electronic device of claim 1, wherein the tasks further comprise:
resizing the selected human body model; and
resizing the 3D sensation map to correspond with the resized selected human body model.

27. The electronic device of claim 1, wherein the tasks further comprise:
offering, via the user interface, a plurality of predefined pain regions that each correspond to a different part of a human body;
detecting, via the user interface, a selection of one of the predefined pain regions; and
automatically generating a pain map in the selected predefined pain region in response to the detecting.

28. The electronic device of claim 1, wherein the tasks further comprise, before the deriving of the 2D sensation map, zooming into a portion of the selected human body model; and wherein the deriving of the 2D sensation map comprises generating a 2D sensation map that is zoomed into the portion of the selected human body model.

29. The medical system of claim 8, wherein the first processing component is further configured to:
resize the selected human body model; and
resize the 3D sensation map to correspond with the resized selected human body model.

30. The medical system of claim 8, wherein the first processing component is further configured to:
offer, via the user interface, a plurality of predefined pain regions that each correspond to a different part of a human body;
detect, via the user interface, a selection of one of the predefined pain regions; and
automatically generate a pain map in the selected predefined pain region in response to the detected selection.

31. The medical system of claim 8, wherein the first processing component is further configured to: zoom into a portion of the selected human body model before the 2D sensation map is produced; and wherein 2D sensation map is produced by generating a 2D sensation map that is zoomed into the portion of the selected human body model.

32. The method of claim 13, further comprising:
resizing the selected human body model; and
resizing the 3D sensation map to correspond with the resized selected human body model.

33. The method of claim 13, further comprising:
offering, via the user interface, a plurality of predefined pain regions that each correspond to a different part of a human body;
detecting, via the user interface, a selection of one of the predefined pain regions; and
automatically generating a pain map in the selected predefined pain region in response to the detecting.

34. The method of claim 13, further comprising: before the 2D sensation map is created, zooming into a portion of the selected human body model; and wherein the representing the 3D sensation map with the 2D sensation map comprises creating a 2D sensation map that is zoomed into the portion of the selected human body model.

35. The portable electronic apparatus of claim 21, further comprising:
means for resizing the selected human body model; and
means for resizing the 3D sensation map to correspond with the resized selected human body model.

36. The portable electronic apparatus of claim 21, further comprising:
means for offering a plurality of predefined pain regions that each correspond to a different part of a human body;
means for detecting a selection of one of the predefined pain regions; and
means for automatically generating a pain map in the selected predefined pain region in response to the detecting.

37. The portable electronic apparatus of claim 21, further comprising:
means for zooming into a portion of the selected human body model and creating a 2D sensation map that is zoomed into the selected portion of the human body model.

* * * * *